(12) United States Patent
Hawkes et al.

(10) Patent No.: US 7,766,947 B2
(45) Date of Patent: Aug. 3, 2010

(54) CERVICAL PLATE FOR STABILIZING THE HUMAN SPINE

(75) Inventors: David T. Hawkes, Pleasant Grove, UT (US); Thomas M. Sweeney, Sarasota, FL (US)

(73) Assignee: Ortho Development Corporation, Draper, UT (US)

( * ) Notice: Subject to any disclaimer, the term of this patent is extended or adjusted under 35 U.S.C. 154(b) by 92 days.

(21) Appl. No.: 10/930,152

(22) Filed: Aug. 30, 2004

(65) Prior Publication Data

US 2005/0033298 A1 Feb. 10, 2005

Related U.S. Application Data

(63) Continuation-in-part of application No. 10/782,740, filed on Feb. 18, 2004, now abandoned, which is a continuation-in-part of application No. 10/757,384, filed on Jan. 13, 2004, now abandoned, which is a continuation of application No. 10/198,525, filed on Jul. 16, 2002, now Pat. No. 6,679,883.

(60) Provisional application No. 60/335,023, filed on Oct. 31, 2001.

(51) Int. Cl.
*A61B 17/70* (2006.01)
(52) U.S. Cl. ...................................... 606/280
(58) Field of Classification Search ............ 606/60, 606/61, 69, 70, 71, 72, 73; 403/52, 76, 78, 403/89
See application file for complete search history.

(56) References Cited

U.S. PATENT DOCUMENTS 2,699,774 A 1/1955 Livingston 3,779,240 A 12/1973 Kondo
4,041,939 A 8/1977 Hall (Continued)

FOREIGN PATENT DOCUMENTS

CA 1329525 9/1994

(Continued)

OTHER PUBLICATIONS

Haid, The Cervical Spine Study Group anterior cervical plate nomenclature, Neurosurg Focus, Jan. 2002, pp. 1-6, vol. 12.

*Primary Examiner*—Eduardo C Robert
*Assistant Examiner*—David Comstock
(74) *Attorney, Agent, or Firm*—Matthew D. Thayne; Stoel Rives LLP

(57) ABSTRACT

A dynamic spinal fixation plate assembly includes a spinal plate, a receiving member, and a fastener resulting in a low profile orthopedic device. The plate may comprise a hole for maintaining the receiving member. The relationship between the receiving member and the plate may allow the plate to adjust during graft settling. The receiving member may be locked to the plate utilizing the mechanical or chemical properties of the device, or the receiving member may be configured to move and rotate freely within the plate hole, even after the fastener has been secured to the bone. The receiving member may have a tapered sidewall defining a through hole to matingly engage the fastener, which may also have a tapered portion forming a tapered lock-fit therebetween. The receiving member may comprise a lip for retaining the fastener within said receiving member.

50 Claims, 8 Drawing Sheets

U.S. PATENT DOCUMENTS

| | | |
|---|---|---|
| 4,388,921 A | 6/1983 | Sutter et al. |
| 4,401,112 A | 8/1983 | Rezaian |
| 4,433,677 A | 2/1984 | Ulrich et al. |
| RE31,628 E | 7/1984 | Allgower et al. |
| 4,484,570 A | 11/1984 | Sutter et al. |
| 4,492,226 A | 1/1985 | Belykh et al. |
| 4,493,317 A | 1/1985 | Klaue |
| 4,501,269 A | 2/1985 | Bagby |
| 4,503,848 A | 3/1985 | Caspar et al. |
| 4,570,618 A | 2/1986 | Wu |
| 4,604,995 A | 8/1986 | Stephens et al. |
| 4,641,636 A | 2/1987 | Cotrel |
| 4,643,178 A | 2/1987 | Nastari et al. |
| 4,651,724 A | 3/1987 | Berentey et al. |
| 4,743,256 A | 5/1988 | Brantigan |
| 4,763,644 A | 8/1988 | Webb |
| 4,794,918 A | 1/1989 | Wolter |
| 4,805,602 A | 2/1989 | Puno et al. |
| 4,834,757 A | 5/1989 | Brantigan |
| 4,863,476 A | 9/1989 | Shepperd |
| 4,878,915 A | 11/1989 | Brantigan |
| 4,887,596 A | 12/1989 | Sherman |
| 4,936,861 A | 6/1990 | Muller et al. |
| 4,946,458 A | 8/1990 | Harms et al. |
| 4,950,269 A | 8/1990 | Gaines, Jr. |
| 4,961,740 A | 10/1990 | Ray et al. |
| 4,966,600 A | 10/1990 | Songer et al. |
| 4,987,892 A | 1/1991 | Krag et al. |
| 5,005,562 A | 4/1991 | Cotrel |
| 5,024,213 A | 6/1991 | Asher et al. |
| 5,026,373 A | 6/1991 | Ray et al. |
| 5,041,113 A | 8/1991 | Biedermann et al. |
| 5,047,029 A | 9/1991 | Aebi et al. |
| 5,053,036 A | 10/1991 | Perren et al. |
| 5,055,104 A | 10/1991 | Ray |
| 5,057,111 A | 10/1991 | Park |
| 5,074,864 A | 12/1991 | Cozad |
| 5,102,412 A | 4/1992 | Rogozinski |
| 5,108,399 A | 4/1992 | Eitenmuller et al. |
| 5,108,446 A | 4/1992 | Wagner et al. |
| 5,116,340 A | 5/1992 | Songer et al. |
| 5,123,926 A | 6/1992 | Pisharodi |
| 5,127,912 A | 7/1992 | Ray et al. |
| 5,127,914 A | 7/1992 | Calderale et al. |
| 5,129,388 A | 7/1992 | Vignaud et al. |
| 5,129,904 A | 7/1992 | Illi |
| 5,147,359 A | 9/1992 | Cozad et al. |
| 5,147,360 A | 9/1992 | Dubousset |
| 5,147,361 A | 9/1992 | Ojima et al. |
| 5,151,103 A | 9/1992 | Tepic et al. |
| 5,152,303 A | 10/1992 | Allen |
| 5,154,718 A | 10/1992 | Cozad et al. |
| 5,171,278 A | 12/1992 | Pisharodi |
| 5,176,678 A | 1/1993 | Tsou |
| 5,176,680 A | 1/1993 | Vignaud et al. |
| 5,180,381 A | 1/1993 | Aust et al. |
| 5,181,917 A | 1/1993 | Rogozinski |
| 5,190,544 A | 3/1993 | Chapman et al. |
| 5,192,321 A | 3/1993 | Strokon |
| 5,192,327 A | 3/1993 | Brantigan |
| 5,201,734 A | 4/1993 | Cozad et al. |
| 5,207,678 A | 5/1993 | Harms et al. |
| 5,209,751 A | 5/1993 | Farris et al. |
| 5,242,445 A | 9/1993 | Ashman |
| 5,242,448 A | 9/1993 | Pettine et al. |
| 5,246,442 A | 9/1993 | Ashman et al. |
| 5,261,909 A | 11/1993 | Sutterlin et al. |
| 5,261,911 A | 11/1993 | Carl |
| 5,263,953 A | 11/1993 | Bagby |
| 5,269,784 A | 12/1993 | Mast |
| 5,281,222 A | 1/1994 | Allard et al. |
| 5,282,801 A | 2/1994 | Sherman |
| 5,290,288 A | 3/1994 | Vignaud et al. |
| 5,290,312 A | 3/1994 | Kojimoto et al. |
| 5,290,494 A | 3/1994 | Coombes et al. |
| 5,300,073 A | 4/1994 | Ray et al. |
| 5,303,718 A | 4/1994 | Krajicek |
| 5,304,179 A | 4/1994 | Wagner |
| 5,306,307 A | 4/1994 | Senter et al. |
| 5,306,309 A | 4/1994 | Wagner et al. |
| 5,312,405 A | 5/1994 | Korotko et al. |
| 5,312,410 A | 5/1994 | Miller et al. |
| 5,318,566 A | 6/1994 | Miller |
| 5,324,290 A | 6/1994 | Zdeblick et al. |
| 5,336,223 A | 8/1994 | Rogers |
| 5,336,240 A | 8/1994 | Metzler et al. |
| 5,344,422 A | 9/1994 | Frigg |
| 5,348,026 A | 9/1994 | Davidson |
| 5,357,983 A | 10/1994 | Mathews |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,370,697 A | 12/1994 | Baumgartner |
| 5,376,125 A | 12/1994 | Winkler |
| 5,380,325 A | 1/1995 | Lahille et al. |
| 5,390,683 A | 2/1995 | Pisharodi |
| 5,395,371 A | 3/1995 | Miller et al. |
| 5,395,374 A | 3/1995 | Miller et al. |
| 5,397,364 A | 3/1995 | Kozak et al. |
| 5,403,314 A | 4/1995 | Currier |
| 5,403,315 A | 4/1995 | Ashman |
| 5,405,391 A | 4/1995 | Hednerson et al. |
| 5,415,658 A | 5/1995 | Kilpela et al. |
| 5,417,690 A | 5/1995 | Sennett et al. |
| 5,423,820 A | 6/1995 | Miller et al. |
| 5,423,825 A | 6/1995 | Levine |
| 5,423,826 A | 6/1995 | Coates et al. |
| 5,425,772 A | 6/1995 | Brantigan |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,480,401 A | 1/1996 | Navas |
| 5,480,437 A | 1/1996 | Draenert |
| 5,484,437 A | 1/1996 | Michelson |
| 5,486,176 A | 1/1996 | Hildebrand et al. |
| 5,489,307 A | 2/1996 | Kuslich et al. |
| 5,489,308 A | 2/1996 | Kuslich et al. |
| 5,496,318 A | 3/1996 | Howland et al. |
| 5,498,263 A | 3/1996 | DiNello et al. |
| 5,501,684 A | 3/1996 | Schlapfer et al. |
| 5,505,732 A | 4/1996 | Michelson |
| 5,507,746 A | 4/1996 | Lin |
| 5,514,180 A | 5/1996 | Heggeness et al. |
| 5,514,184 A | 5/1996 | Doi et al. |
| 5,520,690 A | 5/1996 | Errico et al. |
| 5,522,899 A | 6/1996 | Michelson |
| 5,527,341 A | 6/1996 | Gogolewski et al. |
| 5,531,746 A | 7/1996 | Errico et al. |
| 5,531,751 A | 7/1996 | Schultheiss et al. |
| 5,534,027 A | 7/1996 | Hodorek |
| 5,536,270 A | 7/1996 | Songer et al. |
| 5,536,271 A | 7/1996 | Daly et al. |
| 5,545,165 A | 8/1996 | Biedermann et al. |
| 5,549,608 A | 8/1996 | Errico et al. |
| 5,549,612 A | 8/1996 | Yapp et al. |
| 5,554,157 A | 9/1996 | Errico et al. |
| 5,558,674 A | 9/1996 | Heggeness et al. |
| 5,563,124 A | 10/1996 | Damien et al. |
| 5,569,248 A | 10/1996 | Mathews |
| 5,569,253 A | 10/1996 | Farris et al. |
| 5,571,192 A | 11/1996 | Schönhöffer |
| 5,575,792 A | 11/1996 | Errico et al. |

| | | | | | |
|---|---|---|---|---|---|
| 5,578,033 A | 11/1996 | Errico et al. | 5,681,319 A | 10/1997 | Biedermann et al. |
| 5,578,034 A | 11/1996 | Estes | 5,683,391 A | 11/1997 | Boyd |
| 5,584,834 A | 12/1996 | Errico et al. | 5,683,392 A | 11/1997 | Richelsoph et al. |
| 5,586,984 A | 12/1996 | Errico et al. | 5,683,393 A | 11/1997 | Ralph |
| 4,961,740 A | 1/1997 | Ray et al. | 5,683,394 A | 11/1997 | Rinner |
| 5,591,166 A | 1/1997 | Bernhardt et al. | 5,688,272 A | 11/1997 | Montague et al. |
| 5,593,409 A | 1/1997 | Michelson | 5,688,273 A | 11/1997 | Errico et al. |
| 5,601,553 A | 2/1997 | Trebing et al. | 5,688,274 A | 11/1997 | Errico et al. |
| 5,601,556 A | 2/1997 | Pisharodi | 5,688,279 A | 11/1997 | McNulty et al. |
| 5,603,713 A | 2/1997 | Aust et al. | 5,688,280 A | 11/1997 | Booth, Jr. et al. |
| 5,607,424 A | 3/1997 | Tropiano | 5,690,629 A | 11/1997 | Asher et al. |
| 5,607,425 A | 3/1997 | Rogozinski | 5,690,630 A | 11/1997 | Errico et al. |
| 5,607,426 A | 3/1997 | Ralph et al. | 5,690,631 A | 11/1997 | Duncan et al. |
| 5,607,428 A | 3/1997 | Lin | 5,690,632 A | 11/1997 | Schwartz et al. |
| 5,607,430 A | 3/1997 | Bailey | 5,690,633 A | 11/1997 | Taylor et al. |
| 5,609,592 A | 3/1997 | Brumfield et al. | 5,690,842 A | 11/1997 | Panchison |
| 5,609,593 A | 3/1997 | Errico et al. | 5,693,046 A | 12/1997 | Songer et al. |
| 5,609,594 A | 3/1997 | Errico et al. | 5,693,053 A | 12/1997 | Estes |
| 5,609,596 A | 3/1997 | Pepper | 5,693,100 A | 12/1997 | Pisharodi |
| 5,609,635 A | 3/1997 | Michelson | 5,697,929 A | 12/1997 | Mellinger |
| 5,609,636 A | 3/1997 | Kohrs et al. | 5,697,977 A | 12/1997 | Pisharodi |
| 5,611,800 A | 3/1997 | Davis et al. | 5,700,291 A | 12/1997 | Kuslich et al. |
| 5,611,801 A | 3/1997 | Songer et al. | 5,700,292 A | 12/1997 | Margulies |
| 5,613,967 A | 3/1997 | Engelhardt et al. | 5,702,391 A | 12/1997 | Lin |
| 5,616,144 A | 4/1997 | Yapp et al. | 5,702,392 A | 12/1997 | Wu et al. |
| 5,620,443 A | 4/1997 | Gertzbein et al. | 5,702,393 A | 12/1997 | Pfaifer |
| 5,624,441 A | 4/1997 | Sherman et al. | 5,702,394 A | 12/1997 | Henry et al. |
| 5,626,579 A | 5/1997 | Muschler et al. | 5,702,395 A | 12/1997 | Hopf |
| 5,628,740 A | 5/1997 | Mullane | 5,702,396 A | 12/1997 | Hoenig et al. |
| 5,628,756 A | 5/1997 | Barker, Jr. et al. | 5,702,399 A | 12/1997 | Kilpela et al. |
| 5,630,816 A | 5/1997 | Kambin | 5,702,449 A | 12/1997 | McKay |
| 5,632,747 A | 5/1997 | Scarborough et al. | 5,702,450 A | 12/1997 | Bisserie |
| 5,634,925 A | 6/1997 | Urbanski | 5,702,451 A | 12/1997 | Biedermann et al. |
| 5,643,260 A | 7/1997 | Doherty | 5,702,452 A | 12/1997 | Argenson et al. |
| 5,643,264 A | 7/1997 | Sherman et al. | 5,702,453 A | 12/1997 | Rabbe et al. |
| 5,643,265 A | 7/1997 | Errico et al. | 5,702,454 A | 12/1997 | Baumgartner |
| 5,645,084 A | 7/1997 | McKay | 5,702,455 A | 12/1997 | Saggar |
| 5,645,544 A | 7/1997 | Tai et al. | 5,704,936 A | 1/1998 | Mazel |
| 5,645,549 A | 7/1997 | Boyd et al. | 5,704,937 A | 1/1998 | Martin |
| 5,645,598 A | 7/1997 | Brosnahan, III | 5,707,372 A | 1/1998 | Errico et al. |
| 5,647,873 A | 7/1997 | Errico et al. | 5,709,681 A | 1/1998 | Pennig |
| 5,649,927 A | 7/1997 | Kilpela et al. | 5,709,682 A | 1/1998 | Medoff |
| 5,651,283 A | 7/1997 | Runciman et al. | 5,709,683 A | 1/1998 | Bagby |
| 5,651,789 A | 7/1997 | Cotrel | 5,709,684 A | 1/1998 | Errico et al. |
| 5,653,708 A | 8/1997 | Howland | 5,709,685 A | 1/1998 | Dombrowski et al. |
| 5,653,709 A | 8/1997 | Frigg | 5,709,686 A | 1/1998 | Talos et al. |
| 5,653,763 A | 8/1997 | Errico et al. | 5,713,841 A | 2/1998 | Graham |
| 5,658,289 A | 8/1997 | Boucher et al. | 5,713,899 A | 2/1998 | Marnay et al. |
| 5,658,337 A | 8/1997 | Kohrs et al. | 5,713,900 A | 2/1998 | Benzel et al. |
| 5,658,516 A | 8/1997 | Eppley et al. | 5,713,903 A | 2/1998 | Sander et al. |
| 5,662,653 A | 9/1997 | Songer et al. | 5,713,904 A | 2/1998 | Errico et al. |
| 5,665,088 A | 9/1997 | Gil et al. | 5,713,989 A | 2/1998 | Stücker et al. |
| 5,665,112 A | 9/1997 | Thal | 5,716,355 A | 2/1998 | Jackson et al. |
| 5,665,122 A | 9/1997 | Kambin | 5,716,356 A | 2/1998 | Biedermann et al. |
| 5,667,506 A | 9/1997 | Sutterlin | 5,716,357 A | 2/1998 | Rogozinski |
| 5,667,507 A | 9/1997 | Corin et al. | 5,716,358 A | 2/1998 | Ochoa et al. |
| 5,667,508 A | 9/1997 | Errico et al. | 5,716,359 A | 2/1998 | Ojima et al. |
| 5,668,288 A | 9/1997 | Storey et al. | 5,716,415 A | 2/1998 | Steffee |
| 5,669,909 A | 9/1997 | Zdeblick et al. | 5,716,416 A | 2/1998 | Lin |
| 5,669,910 A | 9/1997 | Korhonen et al. | 5,720,746 A | 2/1998 | Soubeiran |
| 5,669,911 A | 9/1997 | Errico et al. | 5,720,747 A | 2/1998 | Burke |
| 5,671,695 A | 9/1997 | Schroeder | 5,720,748 A | 2/1998 | Kuslich et al. |
| 5,672,175 A | 9/1997 | Martin | 5,720,751 A | 2/1998 | Jackson |
| 5,672,176 A | 9/1997 | Biedermann et al. | 5,722,977 A | 3/1998 | Wilhelmy |
| 5,674,222 A | 10/1997 | Berger et al. | 5,725,588 A | 3/1998 | Errico et al. |
| 5,674,295 A | 10/1997 | Ray et al. | 5,733,285 A | 3/1998 | Errico et al. |
| 5,674,296 A | 10/1997 | Bryan et al. | 5,733,286 A | 3/1998 | Errico et al. |
| 5,676,665 A | 10/1997 | Bryan | 5,735,850 A | 4/1998 | Baumgartner et al. |
| 5,676,666 A | 10/1997 | Oxland et al. | 5,766,254 A | 6/1998 | Gelbard |
| 5,676,701 A | 10/1997 | Yuan et al. | 5,797,912 A | 8/1998 | Runciman et al. |
| 5,676,703 A | 10/1997 | Gelbard | 5,800,435 A | 9/1998 | Errico et al. |
| 5,681,311 A | 10/1997 | Foley et al. | 5,807,396 A | 9/1998 | Raveh |
| 5,681,312 A | 10/1997 | Yuan et al. | 5,817,094 A | 10/1998 | Errico et al. |

| | | |
|---|---|---|
| D402,032 S | 12/1998 | Stone |
| D406,646 S | 3/1999 | Stone |
| 5,876,402 A | 3/1999 | Errico et al. |
| 5,882,350 A | 3/1999 | Ralph et al. |
| 5,888,204 A | 3/1999 | Ralph et al. |
| 5,902,303 A | 5/1999 | Eckhof et al. |
| 5,904,683 A | 5/1999 | Pohndorf et al. |
| 5,910,142 A | 6/1999 | Tatar |
| 5,954,722 A | 9/1999 | Bono |
| 5,968,046 A | 10/1999 | Castleman |
| 6,017,345 A | 1/2000 | Richelsoph |
| 6,022,350 A | 2/2000 | Ganem |
| 6,036,693 A | 3/2000 | Yuan et al. |
| 6,080,193 A | 6/2000 | Hochshuler et al. |
| 6,102,951 A | 8/2000 | Sutter et al. |
| 6,117,173 A | 9/2000 | Taddia et al. |
| 6,129,730 A | 10/2000 | Bono et al. |
| 6,139,550 A | 10/2000 | Michelson |
| 6,152,927 A | 11/2000 | Farris |
| 6,159,213 A | 12/2000 | Rogozinski |
| 6,187,005 B1 | 2/2001 | Brace et al. |
| 6,193,720 B1 | 2/2001 | Yuan et al. |
| 6,193,721 B1 | 2/2001 | Michelson |
| 6,206,881 B1 | 3/2001 | Frigg et al. |
| D440,311 S | 4/2001 | Michelson |
| 6,214,005 B1 | 4/2001 | Benzel et al. |
| 6,224,602 B1 | 5/2001 | Hayes |
| 6,228,085 B1 | 5/2001 | Theken et al. |
| 6,231,610 B1 | 5/2001 | Geisler |
| 6,235,033 B1 | 5/2001 | Brace et al. |
| 6,235,034 B1 | 5/2001 | Bray |
| 6,241,731 B1 | 6/2001 | Fiz |
| 6,258,089 B1 | 7/2001 | Campbell et al. |
| 6,261,291 B1 | 7/2001 | Talaber et al. |
| 6,273,889 B1 | 8/2001 | Richelsoph |
| 6,290,703 B1 | 9/2001 | Ganem |
| 6,293,949 B1 | 9/2001 | Justis et al. |
| 6,306,136 B1 | 10/2001 | Baccelli |
| 6,342,055 B1 | 1/2002 | Eisermann et al. |
| 6,379,354 B1 | 4/2002 | Rogozinski |
| 6,383,186 B1 | 5/2002 | Michelson |
| 6,398,783 B1 | 6/2002 | Michelson |
| 6,402,756 B1 | 6/2002 | Ralph et al. |
| 6,413,259 B1 | 7/2002 | Lyons et al. |
| 6,416,528 B1 | 7/2002 | Michelson |
| 6,428,542 B1 | 8/2002 | Michelson |
| 6,454,771 B1 | 9/2002 | Michelson |
| 6,458,133 B1 | 10/2002 | Lin |
| 6,508,818 B2 | 1/2003 | Steiner et al. |
| 6,527,776 B1 | 3/2003 | Michelson |
| 6,533,786 B1 | 3/2003 | Needham et al. |
| 6,565,571 B1 | 5/2003 | Jackowski et al. |
| 6,572,619 B2 | 6/2003 | Santilli |
| 6,572,622 B1 | 6/2003 | Schäfer et al. |
| 6,575,975 B2 | 6/2003 | Brace et al. |
| 6,602,255 B1 | 8/2003 | Campbell et al. |
| 6,605,090 B1 | 8/2003 | Trieu et al. |
| 6,626,970 B2 | 9/2003 | Campbell et al. |
| 6,656,181 B2 | 12/2003 | Dixon et al. |
| 6,695,846 B2 | 2/2004 | Richelsoph et al. |
| 6,780,186 B2 | 8/2004 | Errico et al. |
| 2001/0007941 A1 | 7/2001 | Steiner et al. |
| 2001/0014807 A1 | 8/2001 | Wagner et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0004660 A1 | 1/2002 | Henniges et al. |
| 2002/0029040 A1 | 3/2002 | Morrison et al. |
| 2002/0045896 A1 | 4/2002 | Michelson |
| 2002/0045897 A1 | 4/2002 | Dixon et al. |
| 2002/0045898 A1 | 4/2002 | Freid et al. |
| 2002/0045899 A1 | 4/2002 | Errico et al. |
| 2002/0058940 A1 | 5/2002 | Frigg et al. |
| 2002/0065517 A1 | 5/2002 | Paul |
| 2002/0077630 A1 | 6/2002 | Lin |
| 2002/0082603 A1 | 6/2002 | Dixon et al. |
| 2002/0111630 A1 | 8/2002 | Ralph et al. |
| 2002/0120271 A1 | 8/2002 | Dixon et al. |
| 2002/0120273 A1 | 8/2002 | Needham et al. |
| 2002/0128655 A1 | 9/2002 | Michelson |
| 2002/0143328 A1 | 10/2002 | Shluzas et al. |
| 2002/0151893 A1 | 10/2002 | Santilli |
| 2002/0151896 A1 | 10/2002 | Ferree |
| 2002/0151899 A1 | 10/2002 | Bailey et al. |
| 2002/0173790 A1 | 11/2002 | Chang et al. |
| 2003/0018335 A1 | 1/2003 | Michelson |
| 2003/0045880 A1 | 3/2003 | Michelson |
| 2003/0078583 A1 | 4/2003 | Biedermann et al. |
| 2003/0105462 A1 | 6/2003 | Haider |
| 2003/0225409 A1 | 12/2003 | Freid et al. |
| 2004/0068319 A1 | 4/2004 | Cordaro |
| 2004/0127896 A1 | 7/2004 | Lombardo et al. |
| 2004/0127899 A1 | 7/2004 | Konieczynski et al. |
| 2004/0260306 A1 | 12/2004 | Fallin et al. |
| 2005/0004574 A1 | 1/2005 | Muckter |
| 2005/0010219 A1 | 1/2005 | Dalton |

FOREIGN PATENT DOCUMENTS

| | | |
|---|---|---|
| DE | 3027148 C2 | 5/1982 |
| DE | 43 23 856 | 10/1994 |
| EP | 0 260 044 | 3/1988 |
| EP | 0 578 320 A1 | 1/1994 |
| EP | 0 778 007 A1 | 6/1997 |
| FR | 2 717 068 | 9/1995 |
| FR | 2 732 887 | 10/1996 |
| FR | 2 736 535 | 1/1997 |
| WO | WO-88/03781 | 2/1988 |
| WO | WO-94/16634 | 8/1994 |
| WO | WO-97/00054 | 1/1997 |
| WO | WO-97/06753 | 2/1997 |

1

CERVICAL PLATE FOR STABILIZING THE HUMAN SPINE

CROSS-REFERENCE TO RELATED APPLICATIONS

This application is a continuation-in-part of U.S. patent application Ser. No. 10/782,740, filed Feb. 18, 2004 now abandoned, entitled "CERVICAL PLATE FOR STABILIZING THE HUMAN SPINE," which is a continuation-in-part of U.S. patent application Ser. No. 10/757,384, filed Jan. 13, 2004 now abandoned, entitled "CERVICAL PLATE FOR STABILIZING THE HUMAN SPINE," which is a continuation of U.S. patent application Ser. No. 10/198,525, filed Jul. 16, 2002, entitled "CERVICAL PLATE FOR STABILIZING THE HUMAN SPINE," now U.S. Pat. No. 6,679,883, which claimed the benefit of U.S. Provisional Application No. 60/335,023, filed Oct. 31, 2001, all of which are hereby incorporated by reference herein in their entireties, including but not limited to those portions that specifically appear hereinafter, the incorporation by reference being made with the following exception: In the event that any portion of any of the above-referenced applications is inconsistent with this application, this application supercedes said portion of said above-referenced application.

STATEMENT REGARDING FEDERALLY SPONSORED RESEARCH OR DEVELOPMENT

Not Applicable.

BACKGROUND OF THE DISCLOSURE

1. The Field of the Invention

The present disclosure relates generally to orthopedic bone fixation devices for stabilizing a plurality of bone segments, and more particularly, but not necessarily entirely, to a bone plate and a bone screw assembly for stabilizing the cervical spine and blocking movement of grafts, and otherwise maintaining the cervical vertebrae in a desired relationship.

2. Description of Related Art

The spine is a flexible, multi-segmented column that supports the upright posture in a human while providing mobility to the axial skeleton. The spine serves the functions of encasing and protecting vital neural elements and provides structural support for the body by transmitting the weight of the body through the pelvis to the lower extremities. Because there are no ribs attached to either the cervical spine or the lumbar spine, they have a relatively wide range of motion.

The spine is made up of bone, intervertebral discs, synovial joints with their articular cartilage, synovial capsules and, as part of the back, is surrounded by supporting ligaments, muscle, fascia, blood vessels, nerves, and skin. As in other areas of the body, these elements are subject to a variety of pathological disturbances: inflammation, trauma, neoplasm, congenital anomalies, disease, etc. In fulfilling its role in the back, the spine can be subjected to significant trauma which plays a dominant role in the etiology of neck and low back pain. Trauma frequently results in damage at the upper end of the lumbar spine, where the mobile lumbar segments join the less mobile dorsal spine. Excessive forces on the spine not only produce life-threatening traumatic injuries, but may contribute to an increased rate of degenerative change.

The cervical spine comprises the first seven vertebrae of the spine, which begin at the base of the skull and end at the upper torso. Because the neck has a wide range of motion and is the main support for the head, the neck is extremely vulnerable to injury and degeneration.

Spinal fixation has become a common approach in treating spinal disorders, fractures, and for fusion of the vertebrae. One common device used for spinal fixation is the bone fixation plate. Generally, there are two types of spinal plates available, (i) constrained plates and (ii) semiconstrained plates. Generally, a constrained plate completely immobilizes the vertebrae and does not allow for graft settling. In contrast, a semiconstrained plate is dynamic and allows for a limited degree of graft settling through micro-adjustments made between the plate and bone screws attaching the plate to the spine perhaps by way of an intervening coupling ring that holds the screws within the plate. The operation of the semiconstrained plate stimulates bone growth. Each type of plate has its own advantages depending upon the anatomy and age of the patient, and the results desired by the surgeon.

A typical bone fixation plate includes a relatively flat, rectangular plate having a plurality of holes formed therein. A corresponding plurality of bone screws may be provided to secure the bone fixation plate to the vertebrae of the spine.

A common problem associated with the use of bone fixation plates is the tendency for bone screws to become dislodged and "back out" from the bone, thereby causing the plate to loosen. Some attempts to provide a screw with polyaxial capabilities to help avoid screw "back out" are known throughout the prior art. However, many of these attempts have resulted in a bone fixation plate having a very large profile and size that can cause irritation and discomfort in the patient's spinal region, or an assembly with multiple parts that must be assembled prior to implantation, which can be laborious and time consuming for surgeons.

In a typical anterior cervical fusion surgery, the carotid sheath and sternocleidomastoid muscles are moved laterally and the trachea and esophagus are moved medially in order to expose the cervical spine. The cervical plate is designed to lie near and posterior to the esophagus. Due to its relative location to the esophagus and other connective tissue, if the bone screw securing the plate to the cervical spine backs out, the bone screw could pierce the esophagus, causing not only pain and infection, but also posing a serious risk of death to the patient. The anti-back out mechanism is important not only to avoid piercing of the esophagus, but also to reduce the profile size of the plate, such that no post-operative difficulty in swallowing is experienced by the patient.

There are several spinal fixation devices known in the prior art. U.S. Pat. No. 6,193,720 (granted Feb. 27, 2001 to Yuan et al.) discloses a cervical spine stabilization device. This cervical spine fixation device requires multiple component parts to provide fixation between a plurality of vertebrae. This device is complex in operation because it requires multiple parts, each of which must be adjusted by the surgeon during surgery, causing extra unnecessary and unwanted labor and time.

U.S. Pat. No. 6,022,350 (granted Feb. 8, 2000 to Ganem) discloses a bone fixation device comprising an elongate link for receiving at least one bone-fastening screw containing a semi-spherical head, which bone-fastening screw passes through an orifice created in the elongate link. The bottom of the elongate link contains a bearing surface that essentially has a circular cross section, allowing the semi-spherical head to be seated therein. The device further includes a plug having a thread suitable for coming into clamping contact against the screw head to hold the head in a desired angular position. This device is characterized by several disadvantages, including the need for a larger profile fixation device in order to allow the semi-spherical bone-fastening screw head and the accompanying plug to fit within the bearing surface. Ganem's larger profile design reduces the effectiveness of the device because of the potential for increased discomfort for the patient.

It is noteworthy that none of the prior art known to applicants provides a spinal fixation device having a low profile size, utilizes few component parts, and provides the surgeon with the ability to manipulate and micro-adjust the fixation device. There is a long felt, but unmet, need for a spinal fixation device which is relatively inexpensive to make, simple in operation and provides a secure interlock between the head of a fastener, such as a bone screw, and the inner sidewall of a receiving member, which is located within a plate hole, that also has a low profile.

The prior art is thus characterized by several disadvantages that are addressed by the present disclosure. The present disclosure minimizes, and in some aspects eliminates, the above-mentioned failures, and other problems, by utilizing the methods and structural features described herein.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the drawings, subsequent detailed description and appended claims.

BRIEF DESCRIPTION OF THE DRAWINGS

The above and other features and advantages of the disclosure will become apparent from a consideration of the subsequent detailed description presented in connection with the accompanying drawings in which.

DETAILED DESCRIPTION

Figure 1:
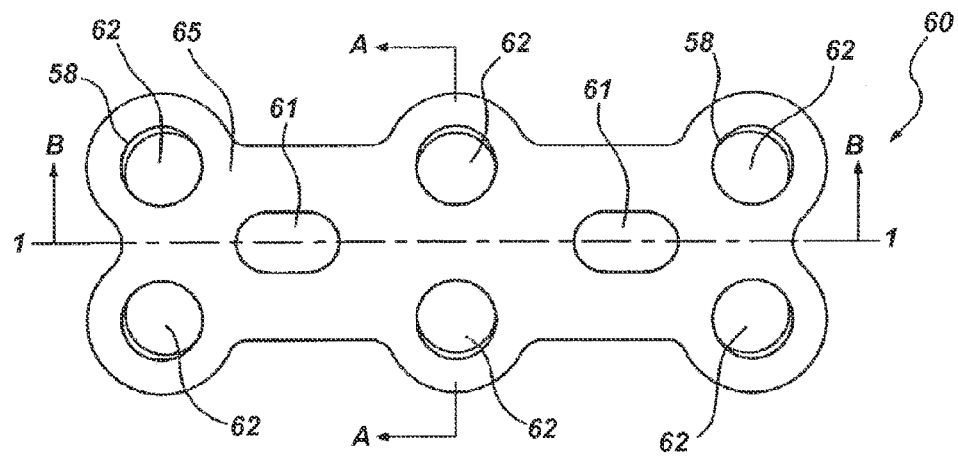
FIG. 1 is a top view of a dynamic spinal plate illustrated with three pairs of holes for implantation purposes, made in accordance with the principles of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the present device and methods for implantation of said device are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

The phrase "interference fit" as used herein shall refer broadly to the concept of a blocking relationship between two members in which a portion of one member abuts or resides in alignment with some portion of the other member, in a manner that contactibly blocks the movement of one member with respect to the other member in at least a first direction.

Figure 2:
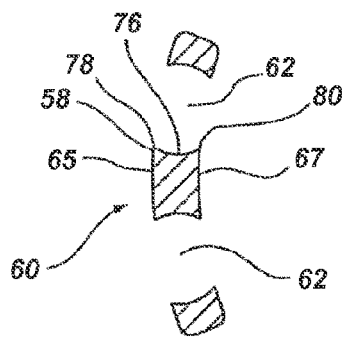
FIG. 2 is a cross-sectional view of the dynamic spinal plate taken along section A-A of FIG. 1.
Figure 3:
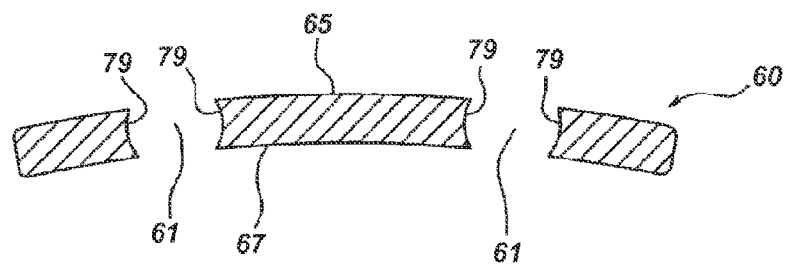
FIG. 3 is a side, cross-sectional view of the dynamic spinal plate taken along section B-B of FIG. 1.

Referring now to the drawings, FIGS. 1-3 illustrate an elongate member in the form of a spinal plate made in accordance with the principles of the present disclosure, and more particularly a cervical plate designated generally at 60. The elongate member 60, also referred to herein as an attachment member, and its component parts may be manufactured from any suitable biocompatible material, including metal, such as titanium, stainless steel, cobalt-chromium-molybdenum alloy, titanium-aluminum vanadium alloy or other suitable metallic alloys, or non-metallic biocompatible materials such as carbon-fiber, ceramic, bio-resorbable materials or if desired any suitable high strength plastic such as an ultra high molecular weight polyethylene. It will be appreciated by those skilled in the art that other biocompatible materials, whether now known or later discovered, may be utilized by the present disclosure, and said biocompatible materials are intended to fall within the scope of the present disclosure.

Figure 7:
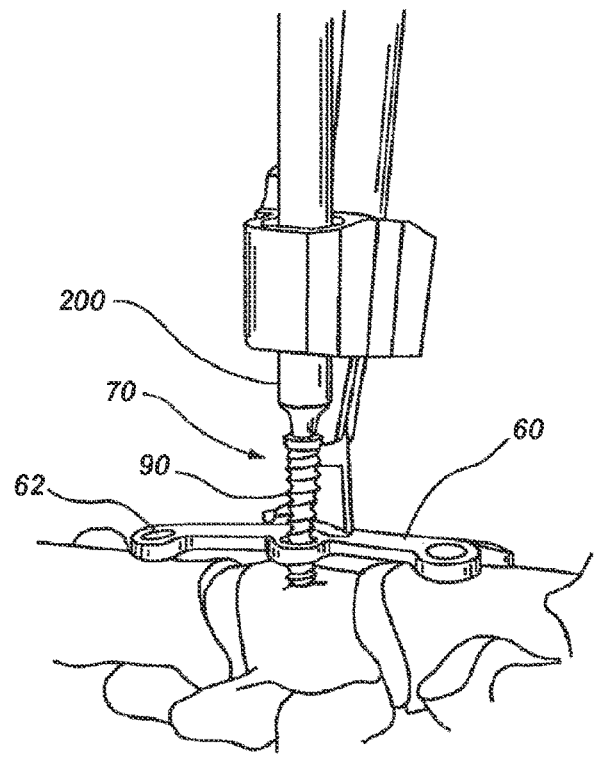
FIG. 7 is a side view of a spinal plate system and a driving instrument inserting a bone screw through a cervical plate and into the cervical spine, made in accordance with the principles of the present disclosure.
Figure 8:
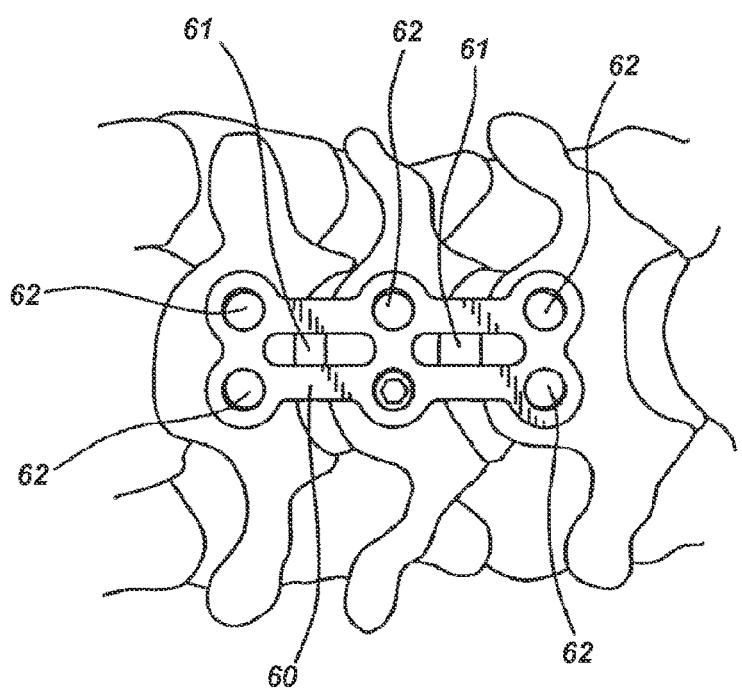
FIG. 8 is a top view of the spinal plate system of FIG. 7, having a single bone screw inserted through a collet or receiving member (not visible), through the plate and into the cervical spine in accordance with the principles of the present disclosure.

The plate 60 may be configured and dimensioned for being installed on the spine, and more particularly on the anterior portion of the cervical spine as illustrated in FIGS. 7 and 8. While the features and principles of the present disclosure are largely illustrated and described herein as a spinal plate 60, it will be appreciated that the spinal plate 60 is merely one example of how the present disclosure may be used and the principles of the present disclosure may be applied to other orthopedic devices, which will be described herein in more detail.

Referring back to FIGS. 1-3, the plate 60 is illustrated as having a top surface 65 and a bottom surface 67, with holes 62 formed in the plate 60 and extending between said top 65 and bottom 67 surfaces. It will be appreciated that each of the holes 62 may be referred to herein as a first opening 62 formed through the attachment member 60, or as a plate hole 62. Further, each of the holes 62, or first openings 62, may be defined by a sidewall. A circumferential edge 58 of each of the holes 62 may define a diameter of each of said holes 62, while surrounding or encircling the openings of the holes 62. It will be appreciated that the diameter of each hole 62, or first opening, may be variable. In other words, the smallest diameter of the hole 62 may be located at either, or both, the top surface 65 and the bottom surface 67 of the plate 60, or attachment member. Conversely, the largest diameter of the hole 62 may be located near a mid-section of said hole 62.

The circumferential edge 58 may further define an exterior boundary of a retaining lip 78, which may be disposed beneath the circumferential edge 58. The plate holes 62 may be circularly shaped and may be configured and dimensioned to accept a receiving member 64 such that the receiving member 64 may be retained by said retaining lip 78 within said hole 62.

While the shape of the holes 62 are illustrated herein as being circular, it should be noted that other shapes could also be used for the holes 62, such as elongated holes, or any other suitably shaped holes 62 that perform functions similar to the circular holes 62 described herein. Accordingly, any suitable shape for holes 62 is useable, whether round, oblong, or even asymmetrical in shape, and each of the above holes 62 is intended to fall within the scope of the present disclosure.

The plate 60 illustrated in FIG. 1 comprises three pairs of holes 62, with each hole 62 of a pair of plate holes 62 residing on either side of longitudinal axis 1-1, and may be used as a 2-level fusion plate. That is, the plate 60 may be sized to span two levels of vertebrae with two discs sandwiched between three successive vertebrae (seen best in FIGS. 7 and 8). As illustrated in FIG. 1, each hole 62 in the pair of plate holes 62 may be spaced apart from its mate such that the plate holes 62 of each pair reside equidistantly on each side of the longitudinal axis 1-1 of FIG. 1. Alternatively, the three pairs of plate holes 62 may be located within the plate 60 such that no particular spacial relationship exists between them. It should be noted that the plate holes 62 may be located within the plate 60 in any suitable arrangement such that the plate holes 62 may be located over a section of vertebral bone for inserting a fastener 70 into the vertebral bone to secure the plate or elongate member 60 to the vertebral bone.

It should be further noted that a 3-level fusion plate (not illustrated in the figures) may be sized to span three intervertebral discs, and may have eight holes 62 or four pairs of holes 62 for connecting the plate 60 to four vertebrae of the spine. It should be noted that the number of holes 62 in the fusion plate 60 may comprise less than a pair of holes per vertebrae spanned and to which the plate 60 may be connected. In other words, in the present disclosure there is no requirement that the plate 60 contain a pair of holes 62 at each level of vertebral fusion. For example, a 3-level fusion plate 60 may contain eight holes 62, or four pair of holes 62, as described above, or the plate 60 may contain less than eight holes 62, and still accomplish a 3-level fusion. For example, the plate 60 may be designed to span four vertebrae, but only include six holes 62 or four holes 62 located either symmetrically or asymmetrically within the plate 60. The same concept holds true for each and every plate 60 sized to span any number of vertebrae of the spine.

It is to be understood that any size or level of intervertebral fusion may be accomplished by the disclosure, by modifying the plate 60 to be of any size to fuse the desired number of vertebrae. For example, to fuse a greater number of vertebrae additional holes 62 may be added and the plate 60 elongated. Conversely, to fuse less vertebrae the holes 62 may be reduced in number and the plate 60 may be decreased in size. It should be noted that when modifying the plate 60, it is the size of the plate 60 that defines how many vertebrae may be fused, and one of skill in the art can readily identify the appropriate number of holes 62 required for securing said plate 60 to the appropriate number of vertebrae of the spine.

Figure 4:
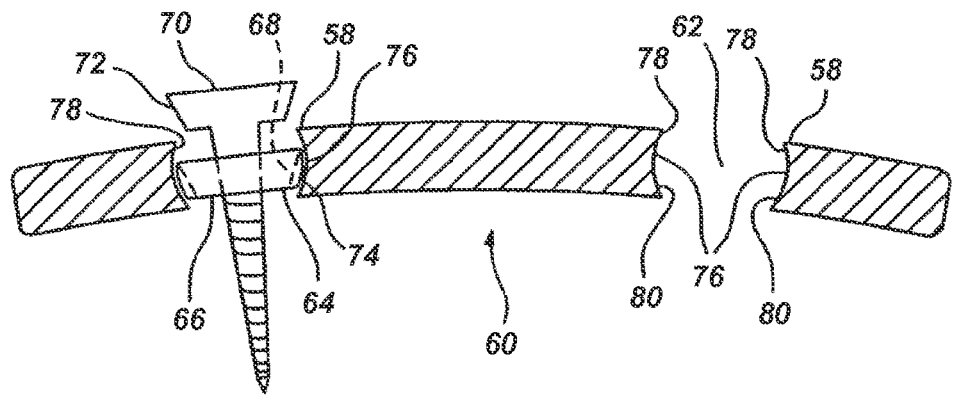
FIG. 4 is a schematic, side view of the dynamic spinal plate taken along section A-A of FIG. 1, illustrated in connection with a receiving member and a bone screw disposed within said spinal plate.

As illustrated in FIGS. 2 and 4, the retaining lip 78, sometimes referred to herein as a retaining member or a means for retaining a receiving member 64, may extend laterally from the plate holes 62 and may be formed near or as an extension of the top surface 65 of the plate 60, and the retaining lip 78 may be associated with the circumferential edge 58. Because the receiving member 64 may be designed and sized to move within the plate hole 62, the retaining lip 78 may function to maintain said receiving member 64 within the plate hole 62 by acting as a retaining barrier, such that the receiving member 64 may contactibly engage the retaining lip 78 to thereby prevent the receiving member 64 from exiting the plate hole 62. It will be appreciated that the retaining lip 78 may extend completely around the entire opening of the plate hole 62, or the retaining lip 78 may be modified such that the retaining lip 78 only extends partially around the opening of the plate hole 62.

Referring again to FIG. 1, through holes 61 may be located in the center portion of the plate 60 along the longitudinal axis 1-1 of said plate 60 for the surgeon's convenience in adjusting the plate 60 to the desired position on the spine. The through holes 61 may be elongated to allow settling or subsidence of the bone graft. The through holes 61 may have a retaining lip 79, as illustrated in FIG. 3, which may be similar to retaining lip 78 surrounding at least a portion of the plate hole 62, or there may be no retaining lip 79 present at all (a condition not shown in the figures). In the latter case, there would be only a circumferential edge similar to the circumferential edge 58 surrounding the plate hole 62.

Figure 5:
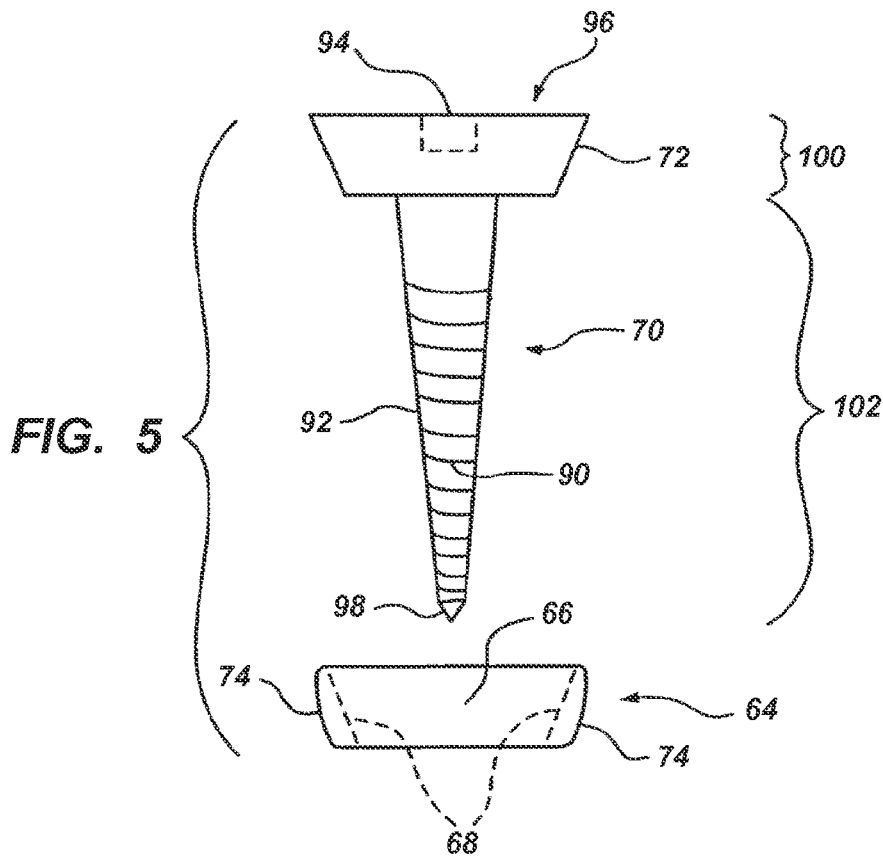
FIG. 5 is an enlarged, exploded side view of the bone screw and receiving member illustrated in FIG. 4.

Referring now to FIG. 5, an enlarged, exploded view of one embodiment of a fastener 70 with a receiving member 64 is illustrated, wherein the fastener 70 may comprise a first portion 100 and a second portion 102. The first portion 100 may comprise a head 96 having a tapered section 72. The head 96 may include a recess 94 formed within a top surface thereof for receiving an instrument 200 (seen best in FIG. 7). It will be appreciated that the instrument 200 may be configured for driving the fastener 70 into the vertebral bone. It should be noted that the tapered section 72 may be formed on the full length of the head 96 as illustrated in FIG. 5, or the tapered section 72 may be formed on a portion of the head 96. It will be appreciated that the tapered section 72 of the first portion 100 may be located on any suitable section of the fastener 70, including the head 96, such that the tapered section 72 may mate with a tapering sidewall 68 defining a tapered section of the receiving member 64. Any such modification is contemplated by and intended to fall within the scope of the present disclosure.

The second portion 102 may comprise a shaft 92, wherein the shaft 92 may contain threads 90, and a tip 98. As used herein, fastener 70 may sometimes be referred to as a screw, bone screw, or as a means for attaching the elongate member 60 to at least one human vertebra. It should be noted, however, that the fastener 70 may be a bone screw, bolt, threadless pin, or any other suitable fastener for attaching the elongate member 60 to at least one human vertebra. It will be appreciated that the fastener 70 of the present disclosure may be any fastener described herein, or any fastener that is known, or that may become known in the future, in the art for attaching the elongate member 60 to at least one vertebra of the spine.

Figure 6:
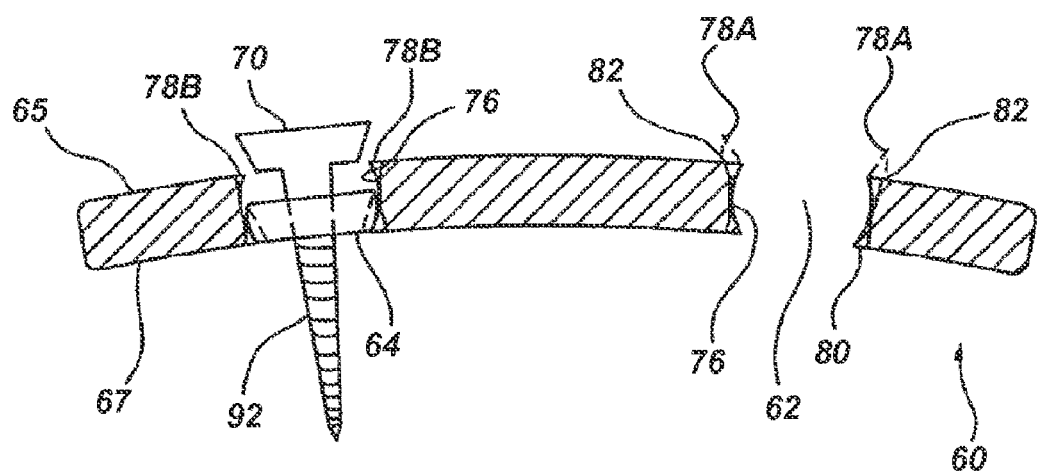
FIG. 6 is a schematic, side view of the dynamic spinal plate taken along section A-A of FIG. 1, illustrating another embodiment of a retaining lip.

Referring now to FIGS. 4, 5, and 6, the plate 60 may be designed to achieve a "constrained" or "semiconstrained" level of stabilizing support determined, in part, by the relationship between each hole 62 and a corresponding receiving member 64. It will be appreciated that the receiving member 64 may sometimes be referred to herein as a means for receiving a fastener 70. While the receiving member 64 is illustrated herein as being a circular ring, it should be noted that other shapes could also be used for the receiving member 64 such as oblong, square, polygonal or any other suitable shape, and any receiving member that performs functions the same as or similar to the receiving member 64 described herein is intended to fall within the scope of the present disclosure. Accordingly, any suitable shape for the receiving member 64 is useable, including but not limited to round, oblong, square, polygonal or even asymmetrical shapes.

The receiving member 64 may include a through-passage 66, which may be defined by a tapering wall, such as frustoconical, tapered sidewall 68. It will be appreciated that the through-passage 66 may also be referred to herein as a first aperture 66, which may be formed through the receiving member 64. Further, the sidewall 68 may further be characterized as a Morse-tapered sidewall. The tapered section 72 of the fastener 70 may be designed to lockably mate with the tapered sidewall 68 of the through passage 66 of the receiving member 64 in a friction fit. The mating engagement between the tapered section 72 and the sidewall 68 may be characterized as self-locking. It should be noted that the taper angle of the sidewall 68 of the receiving member 64 and the taper angle of tapered section 72 of the fastener 70 may be any suitable taper angle such that a self-locking taper may be formed. It will be appreciated that the receiving member 64 may be configured such that it is not caused to substantially expand responsive to the fastener 70 being inserted into the receiving member 64. In other words, the tapered section 72 of the fastener 70 in this embodiment is not intended to cause substantial expansion of said receiving member 64, such that the receiving member 64 does not engage the sidewall 68 of the receiving member 64. Rather, entry of the tapered section 72 of the fastener 70 into the receiving member 64 does not cause the receiving member 64 to substantially expand. However, it should be noted that the receiving member 64 may, if desired, be configured with a slit, gap, or other mechanism for expanding and contracting said receiving member 64. It is to be understood that the receiving member 64 of the present disclosure may be any of the receiving members described herein, or any receiving member that is known, or that may become known in the future, in the art for receiving a fastener thereinto to thereby attach the fastener to the elongate member.

The plate 60 of the present disclosure may be classified as a "restricted backout" plate, wherein the receiving member 64 essentially locks the fastener 70 to the plate 60 such that fastener 70 backout is restricted. This function, and the structure to support it, are explained below in more detail.

Restricted backout systems, such as the embodiments found in the present disclosure, may be classified into two subcategories: (i) constrained plates and (ii) semiconstrained plates. In a restricted backout plate, the fastener 70 may either be fully constrained and locked with respect to the plate 60 such that substantially no movement may be allowed in the fastener-plate interface, or alternatively the fastener 70 may be allowed to rotate or translationally move in relation to the plate 60 in a semiconstrained manner that enables a plurality of angular orientations in which the fastener 70 may be implanted into the spine. A plate 60 that restricts backout and is semiconstrained may allow each fastener 70 and receiving member 64 combination to rotate within the hole 62 about the longitudinal axis of the fastener 70, or may allow each fastener 70 and receiving member 64 combination to slide within the hole 62 in a back-and-forth translational manner, or the plate 60 may allow a combination of the two, allowing some fastener 70 and receiving member 64 combinations to rotate and others to slide translationally. By operation of these structural and functional characteristics, semiconstrained systems may permit controlled subsidence of the plate 60. The present disclosure includes a novel, unique design having aspects of a semiconstrained plating system that allows for both rotational motion and translational motion.

The receiving member 64 may include an arcuate or curved exterior surface 74, which may also be described as a convex exterior surface 74, that fits within and complements an arcuate or curved interior surface 76 of the holes 62, which may also be described as a concave interior surface 76. The receiving member 64 may be designed such that the convex exterior surface 74 can be either fully engaged or partially engaged with the corresponding concave interior surface 76 of the hole 62. In either case, the fastener 70 may be essentially locked to the plate 60.

The receiving member 64 of the present disclosure includes multiple embodiments. In a first "constrained plate" embodiment, the receiving member 64 may be locked to the plate 60 as the fastener 70 is tightened into a corresponding vertebral bone and secured to the receiving member 64. The structure to accomplish this locking feature may subsist in the receiving member 64, and the receiving member 64 may comprise a rough surface finish on the exterior surface 74, such that when the fastener 70 is inserted into the through passage 66 of the receiving member 64 and secured thereto, said receiving member 64 may be locked to the plate 60 by way of the rough surface finish. As used herein, the phrase "rough surface finish" may be defined as a surface having textural inequalities, or ridges, or projections, while the term "smooth" may be defined as having a continuous even surface without any textural inequalities, or ridges, or projections detectable by an average human observer. The rough surface described above may be mechanical or chemical and may be used to create the locking mechanism between the receiving member 64 and the plate 60.

The mechanical lock may occur by way of the receiving member 64 having a rough surface finish to thereby engage in an enhanced frictional engagement with the corresponding interior surface 76 of the hole 62. The interior surface 76 may have a smooth surface finish, or alternatively the interior surface may have a rough surface finish. Thus, the surface roughness of one or both of those components may provide the mechanical qualities sufficient to cause the receiving member 64 to essentially lock to the plate 60 by way of a friction fit.

Another manner in which the receiving member 64 may be essentially locked to the plate 60 in a constrained manner is through chemical properties that may be present in, or added to, the surface of one, or both, of the receiving member 64, and the hole 62. More specifically, chemical properties may be present in or added to the exterior surface 74 of the receiving member 64, or to the interior surface 76 of the hole 62, or to both, as known and understood by those of ordinary skill in the art. For example, a common material used to manufacture orthopedic devices is titanium or any of its alloys. When two pieces of titanium are placed in close proximity together, the chemical properties associated with titanium can be used to essentially lock the two pieces together.

In another illustrative "constrained plate" embodiment for essentially locking the receiving member 64 to the plate 60, the receiving member 64 must be large enough to remain in contact with the interior surface 76 of the hole 62. Such a contact may be accomplished using a difference in the radii of curvature of said receiving member 64 and said interior surface 76 of the hole 62, such that the difference in radii of curvature between those two components creates a lock.

It will be appreciated that the sidewall of the hole 62 may comprise a first curve forming the interior surface 76. Further, the exterior surface 74 of the receiving member 64 may comprise a second curve. The first curve may be substantially the same as, or different than, the second curve. When the first curve is different than the second curve a zone of contact may be created between the sidewall of the hole 62 and the convex exterior surface 74 of the receiving member 64, thereby substantially locking the receiving member 64 to the plate 60.

More specifically, the lock may occur at a zone of contact corresponding to the difference in the radii of curvature between the exterior surface 74 of the receiving member 64 and the interior surface 76 of the hole 62. The zone of contact may include a discrete circumferential contact line, or a wider circumferential band of contact that would be wide enough not to be considered a line of contact. Thus, the receiving member 64 may be maintained within the hole 62 because of the difference in the radii of curvature between components.

Referring now to an alternative "semiconstrained plate" embodiment, in which the convex exterior surface 74 of the receiving member 64 may be partially engaged with the corresponding concave interior surface 76 of the hole 62, or even removed from such engagement by a smaller design of the receiving member 64. The receiving member 64 may be designed to be small enough to remain movable within the plate hole 62 during partial engagement such that (i) if the receiving member 64 is in contact with the concave interior surface 76 such contact is a semiconstrained, movable, dynamic frictional contact; or (ii) only a portion of the convex exterior surface 74 of the receiving member 64 resides in contact with the concave interior surface 76 of the plate hole 62; or (iii) the receiving member 64 may be designed to not even touch the concave interior surface 76 at all and may be retained only by the retaining lip 78. In any of these alternative structural embodiments, the receiving member 64 may be rotated and moved translationally within the plate hole 62 in a "semiconstrained" manner even after the tapered section 72 of the fastener 70 is inserted into and engages the tapered sidewall 68 of the receiving member 64, and even after the receiving member 64 and fastener 70 combination have been attached to the bone of the spine. This partially engaged, "semiconstrained" relationship between the receiving member 64 and the interior surface 76 of the plate hole 62 may permit micro-adjustments of the plate 60 on the spine.

As described above in relation to the "semiconstrained plate" system, the receiving member 64 may be designed to be rotated within the plate hole 62 such that the receiving member 64 may move freely. Such "semiconstrained" embodiments may be accomplished with or without a match of radii of curvature between the exterior surface 74 of the receiving member 64 and the interior surface 76 of the plate hole 62, by designing the size of the plate hole 62 to be large enough to permit "semiconstrained" movements, or the receiving member 64 may be designed to be small enough to permit the member 64 to move in a rotational and translational manner. In such embodiments, the exterior surface 74 of the receiving member 64 and the interior surface 76 of the plate hole 62 may both be smooth. Additionally, the radii of curvature of the receiving member 64 and the interior surface 76 of the plate hole 62 may be configured to match each other, without regard to whether or not the receiving member 64 is engaged with the interior surface 76. The above configurations permit rotation and also slight translational movement of the receiving member 64.

The ability of the receiving member 64 to move within the hole 62 may permit the entire plate 60 to controllably subside or settle. The slight movement allowed between the hole 62 and the receiving member 64 may define the "semiconstrained" state of the plate 60. In order for the receiving member 64 to be partially engaged with the hole 62 and ultimately with the plate 60, the receiving member 64 may be smaller than the corresponding interior of the hole 62 in order to allow the semiconstrained movement. However, the receiving member 64 should not be so small as to permit the receiving member 64 to slide past the retaining lip 78 or a lower rim 80 and separate itself from the plate 60.

Likewise, the receiving member 64 and the hole 62 may have a geometry such that the receiving member 64 may be movable within the hole 62, but cannot flip over itself, or flip one-hundred and eighty (180) degrees from its original position, with respect to a horizontal axis, while it is maintained within the hole 62. Thus, the retaining lip 78 may be able to maintain each embodiment of the receiving member 64 without changing the shape or design of the retaining lip 78. However, it will be appreciated that the shape or design of the retaining lip 78 may be modified by one of ordinary skill in the art without departing from the scope of the present disclosure.

Further, the present disclosure allows the receiving member 64 to lock in one-step with the fastener 70, thereby permitting the surgeon to quickly and efficiently insert the fastener 70 into the spine without undue delay. Because the receiving member 64 may be pre-installed within hole 62 during the manufacturing process or prior to surgery, the surgeon may only need to implant the fastener 70 in the desired location of the vertebra in order to attach the entire plate assembly to the spine. This may be accomplished by inserting the shaft 92 of the fastener 70 through the throughpassage 66 of the receiving member 64 and engaging the tapered interlock fit between the tapered section 72 of the fastener 70 and the tapered sidewall 68 of the receiving member 64, as described above.

Once the fastener 70 has been locked within the receiving member 64, which receiving member 64 may be located within each hole 62 of the plate 60, and secured to an appropriate bone of the spine, the plate 60 is positioned in a semiconstrained state. Thus, some movement between the receiving member 64 and the hole 62 may be permitted by the movable position of the arcuate-exterior surface 74 of the receiving member 64 within the concave-interior surface 76 of the hole 62. As such, the plate 60 may be attached to the spine, and yet may be allowed to settle into a position of stability. The slight movements permitted between the receiving member 64 and the plate 60 permit micro-adjusting, which may reduce the mechanical stress transferred between the plate 60 and the human spine to which it is attached.

It will be appreciated that the receiving member 64 may be configured and dimensioned such that the diameter of the receiving member 64, at its widest point, may be large enough in size to inhibit the receiving member 64 from exiting the confines of the plate hole 62.

Installation of the receiving member 64 within the plate 60 may be accomplished at room temperature due, at least in part, to the elasticity of the material used to manufacture both the receiving member 64 and the plate 60. Room temperature installation may be achieved by elastic deformation of the receiving member 64 and components of the plate 60. The term "elastic deformation" may be defined herein as the deformation of a body in which the applied stress is small enough so that the object retains its original dimensions once the stress is released.

It is important to note that the receiving member 64 and the plate 60 may elastically deform and may not undergo substantial plastic deformation. The term "plastic deformation" may be defined herein as the substantial deformation of a body caused by an applied stress which remains after the stress is removed. It will be appreciated that the stresses causing elastic deformation, to which the receiving member 64 and the plate 60 may be subjected, may also cause a slight amount of plastic deformation in actuality, but such slight amount of plastic deformation does not diminish the function of the receiving member 64 or the plate 60. However, as defined herein, the receiving member 64 and the plate 60 do not undergo substantial plastic deformation.

The receiving member 64 and the hole 62 may be configured and dimensioned so as to provide for installation at room temperature by sizing the receiving member 64 to an appropriate dimension relative to the hole 62, such that when a sufficient force is applied to the receiving member 64, said receiving member 64 and a portion of the plate 60 elastically deform. Once the receiving member 64 is inserted into the hole 62, the force is released and the components each go back to their original size. Once installed, the receiving member 64 may be maintained in the hole 62 by the retaining lip 78. It is important to note that the installation forces placed on the receiving member 64 and the plate 60, which cause elastic deformation, are larger than the forces placed on said receiving member 64 after installation of the complete device on the cervical spine. Therefore, the receiving member 64 may be maintained in the hole 62 by the retaining lip 78 without being forced out of the plate 60 by the naturally occurring forces found in the cervical spine.

Another method of installing the receiving member 64 within the plate hole 62 may occur during the manufacturing process. For example, cooling the receiving member 64 to a sufficient temperature that effectively causes contraction of said receiving member 64 may allow the receiving member 64 to be installed within the plate hole 62. It will be appreciated that cooling may cause the receiving member 64 to contract to a size that is small enough such that the receiving member 64 may be slightly smaller than the opening in the plate hole 62, thereby effectuating the installation of said receiving member 64 within the plate hole 62.

Insertion of the receiving member 64 into the plate hole 62 through cooling may include the following steps. First, inserting the receiving member 64 into liquid nitrogen, waiting a sufficient period of time for contraction of said receiving member 64 to begin, and removing the receiving member 64 from the liquid nitrogen after sufficient contraction of the receiving member 64 has occurred. Second, inserting the contracted receiving member 64 through the top of the plate hole 62 into an interior volume of said plate hole 62, and permitting the receiving member 64 to warm to room temperature, thereby causing expansion of the receiving member 64 to its original shape and size.

The period of time to accomplish the step of cooling the receiving member 64 to a sufficient temperature, to thereby cause the contraction of said receiving member 64, depends upon the properties of the material used to form the receiving member 64 and may be determined by one of ordinary skill in the art. Therefore, it will be appreciated that one of ordinary skill in the art, having possession of this disclosure, could determine the sufficient temperature and time to cause contraction of the receiving member 64 without undue experimentation.

It should be noted that, in addition to liquid nitrogen, any substance for, or method of, cooling the receiving member 64 to a sufficient temperature to cause contraction may be used for contracting the receiving member 64. It should also be noted that the receiving member 64 may be manufactured from any suitable biocompatible material, including metal, such as titanium, stainless steel, cobalt-chromium-molybdenum alloy, titanium-aluminum vanadium alloy, or other suitable metallic alloys, or non-metallic biocompatible materials such as carbon-fiber, ceramic, bio-resorbable materials or if desired any suitable high strength plastic such as an ultra high molecular weight polyethylene. It should likewise be noted that the cooling of the receiving member 64 and subsequent placement into the plate hole 62 is only illustrative of one method of installation that may occur during the manufacturing process, which may be implemented by the present disclosure. It will be appreciated that other methods of manufacture may also be used to accomplish the same or similar results, without departing from the scope of the present disclosure.

After installation and subsequent warming, the receiving member 64 may expand back to its original shape and size, after which the retaining lip 78 may function to maintain the receiving member 64 in the plate hole 62, thereby retaining the receiving member 64. The retaining lip 78 may cooperate with a lower rim 80 to retain the receiving member 64 within the plate hole 62. It will be appreciated that the lower rim 80 may extend laterally from the bottom surface 67 of the plate 60, thereby precluding the receiving member 64 from advancing completely through the plate hole 62. Thus, the lower rim 80 may provide a surface for the receiving member 64 to contact such that said receiving member 64 may be maintained within the plate hole 62 in conjunction with the retaining lip 78.

It should be noted that other embodiments of the retaining lip 78 are contemplated by the present disclosure, such as a depressable retaining lip 78 (seen best in FIG. 6). The depressable retaining lip 78 may be initially upright in an open position, referred to and illustrated in phantom-line as item 78A of FIG. 6, and may have a pivot point 82. The pivot 82 may permit the retaining lip 78 to be depressed downwardly, with respect to the plate 60, into a lateral, closed position 78B. The process or method of installing the receiving member 64 into the plate hole 62 utilizing the depressable retaining lip 78 may include the following. Inserting the receiving member 64 into the corresponding plate hole 62 with the retaining lip 78 in the open position 78A. After the receiving member 64 has been inserted into the plate hole 62, the retaining lip 78 may be depressed into the closed position 78B, thereby retaining the receiving member 64. It will be appreciated that the depressable retaining lip 78 functions similarly to the retaining lip 78 illustrated in FIG. 4.

It will be appreciated that the depressable retaining lip 78 of the present embodiment, illustrated in FIG. 6, does not require the above described installation process of cooling the receiving member 64 to install said receiving member 64 within the plate hole 62. The reason, at least in part, is because of the depressability of the retaining lip 78, which can be opened and closed to permit the entrance of the receiving member 64. The depressable retaining lip 78 may permit the receiving member 64 to be either pre-installed during manufacturing, or installed by a surgeon or surgical staff member prior to, or at the time of, surgery.

In accordance with the features and combinations described above, a useful method of implanting the dynamic spinal bone fixation plate assembly onto a patient's spine includes the steps of:

(a) locating the spinal plate 60 on the patient's spine;

(b) inserting a driving tool 200 into the recess 94 formed in the head 96 of the fastener 70;

(c) inserting the shaft portion 92 of the fastener 70 through the receiving member 64 until the tip 98 engages the bone;

(d) securing the fastener 70 to the bone; and (e) advancing the fastener 70 until the tapered 72 section of the fastener 70 mates with the corresponding tapered sidewall 68 of the receiving member 64, thus locking the fastener 70 to the plate 60.

It is to be understood that the present disclosure is applicable to any implant device or assembly for which the advantages of the disclosure can be used. For example, in addition to a spinal fixation apparatus, the disclosure may also be applied to serve in the form of a fastener-receiving member locking interface as part of the mechanics to lock an acetabular cup to a pelvis, or to lock a tibial tray to a tibial plate, or to lock stabilization plates to long bones, or as part of maxillo facial applications, or any suitable application.

Figure 9:
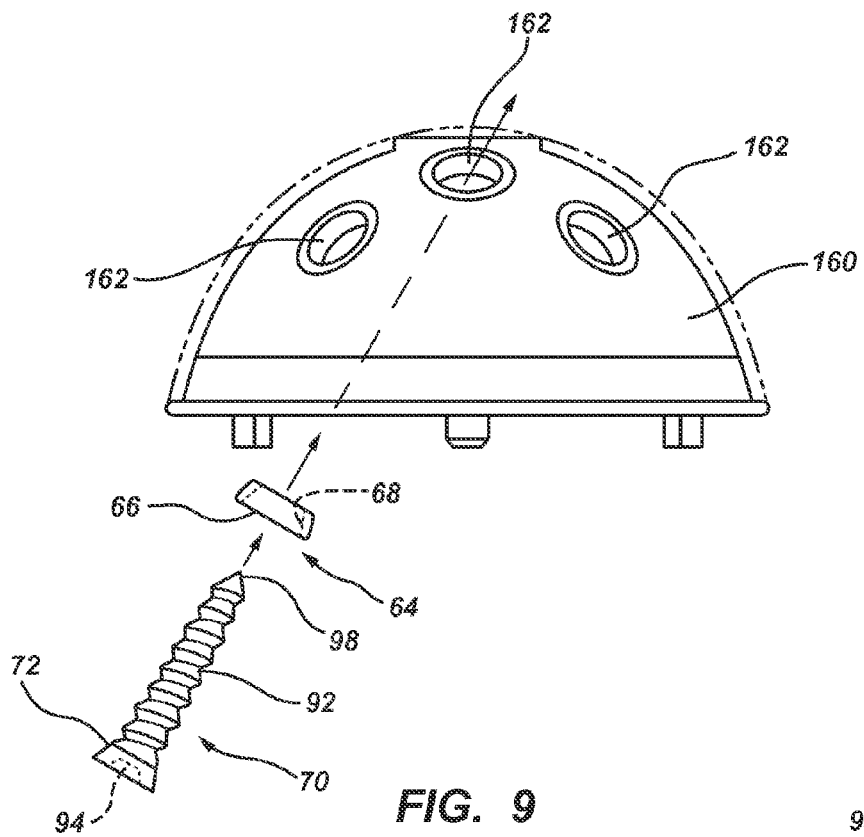
FIG. 9 is an exploded, side view of an alternative embodiment of the present disclosure illustrating a bone screw, a collet or receiving member, and an acetabular cup, made in accordance with the principles of the present disclosure.
Figure 10:
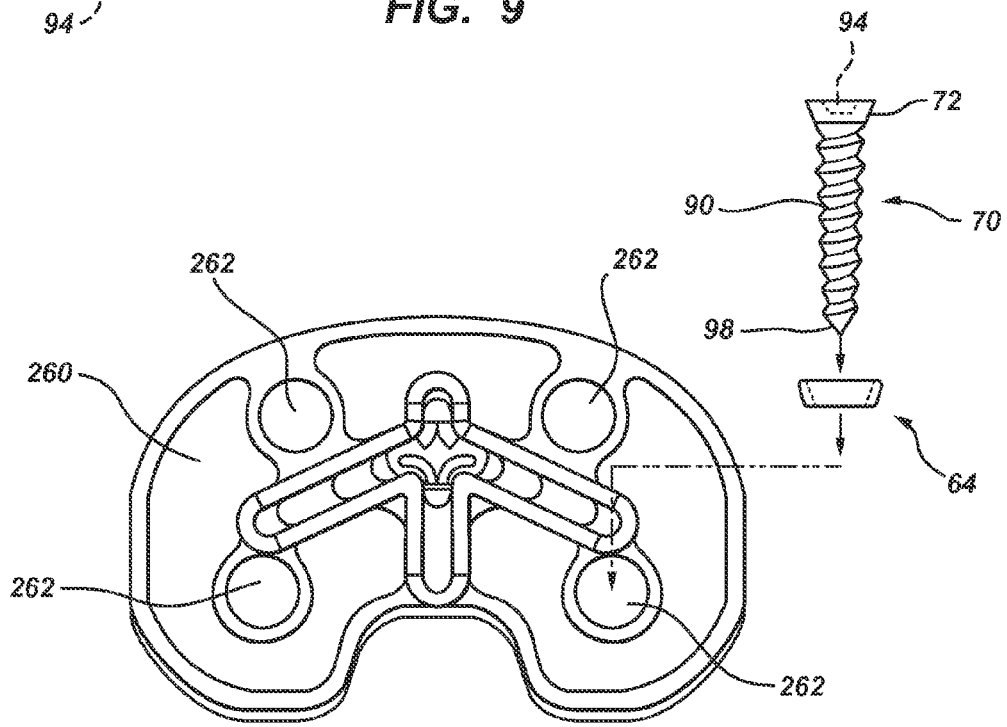
FIG. 10 is a top view of an alternative embodiment of the present disclosure illustrating a bone screw, a collet or receiving member, and a tibial implant, made in accordance with the principles of the present disclosure.

Turning now to FIGS. 9 and 10, wherein like reference numerals represent like structure in previous embodiments. FIG. 9 illustrates an alternative embodiment of the present disclosure as described in relation to the acetabular cup. FIG. 9 is an exploded view of a fastener 70, a receiving member 64 and an alternative embodiment of an attachment member illustrated as an acetabular cup 160. In the present embodiment, the acetabular cup 160 may comprise at least one hole 162 configured for maintaining the receiving member 64 within the acetabular cup 160. The fastener 70, illustrated as a bone screw, may be configured for securing the acetabular cup 160 to the bone. The receiving member 64 and the fastener 70 may, therefore, be used with the acetabular cup 160 in accordance with the principles of the present disclosure, described more fully above.

FIG. 10 is an exploded view of another embodiment of the present disclosure. FIG. 10 specifically illustrates the fastener 70, the receiving member 64 and another alternative embodiment of the attachment member illustrated as a tibial tray 260. The tibial tray 260 comprises at least one tray hole 262 similar to the hole 62 described in relation to the spinal plate 60 and the acetabular cup 160. Essentially, the structural features and principles described above in relation to the spinal plate 60 are also applicable to the tibial tray 260. Therefore, it should be noted that the features and principles of the present disclosure may be applied not only to the spinal plate 60, but also to the acetabular cup 160, the tibial tray 260 as well as other orthopedic devices not illustrated herein.

Figure 11:
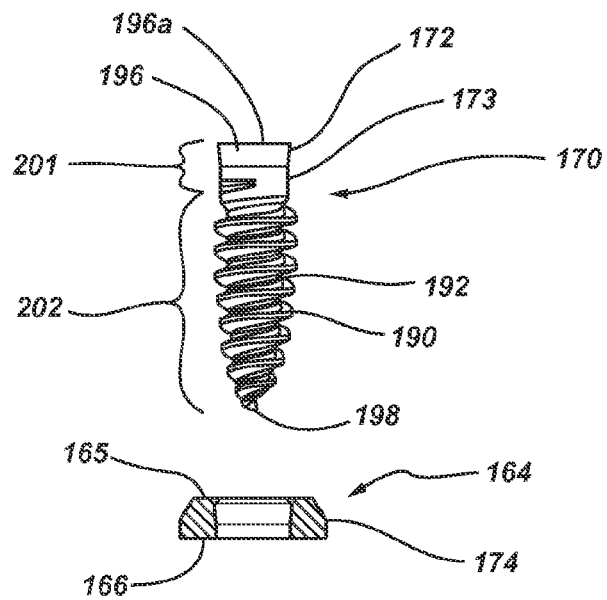
FIG. 11 is an exploded, side view of an alternative embodiment of the present disclosure illustrating a bone screw, and a cross-sectional view of a receiving member, made in accordance with the principles of the present disclosure.
Figure 12:
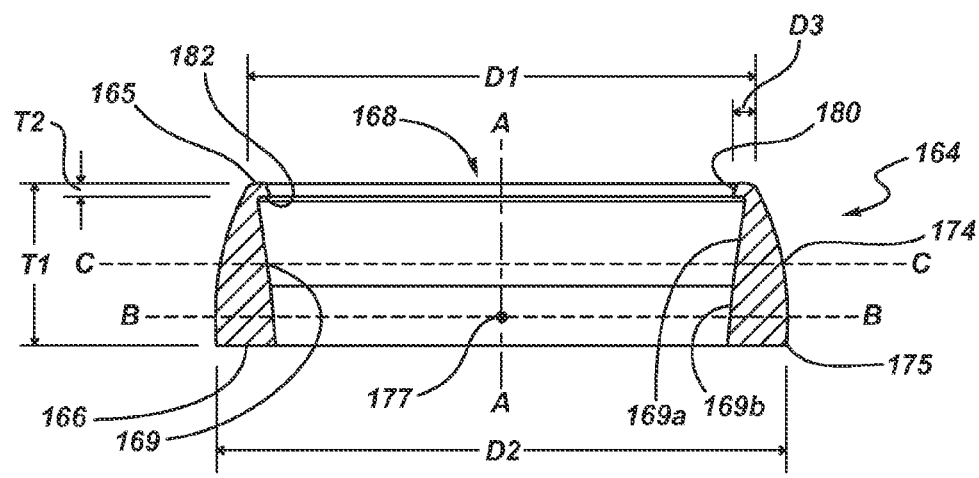
FIG. 12 is an enlarged, side cross-sectional view of the receiving member of FIG. 11, made in accordance with the principles of the present disclosure.
Figure 13:
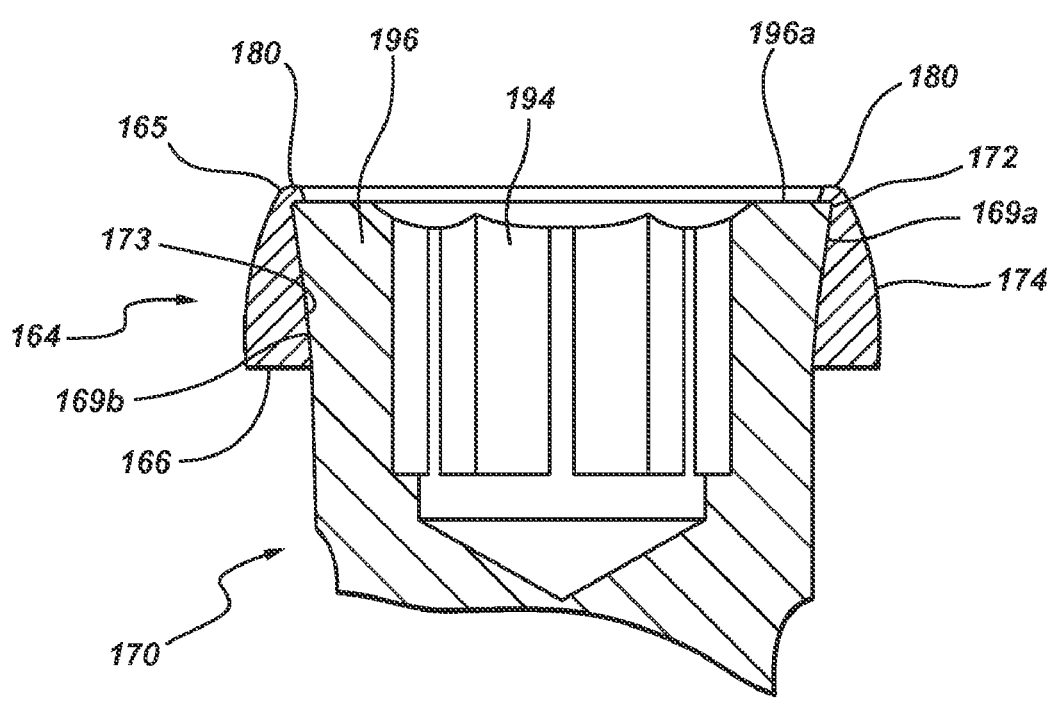
FIG. 13 is an enlarged, side cross-sectional view of the bone screw having been inserted into the receiving member, in accordance with the principles of the present disclosure.

Referring now to FIGS. 11-13, applicants have noted that there may be occurrences that may potentially cause the fasteners 70 and 170 to backout from the bone, and to backout from the receiving members 64 and 164 to which the fasteners 70 and 170 may have been secured, however infrequent. Even with the rarity in which such backout of the fasteners 70 and 170 may occur, due to the strength of the taper lock between the fasteners 70 and 170 and the receiving members 64 and 164, there may be situations where the taper lock may still not provide sufficient locking strength. Applicants have, thus, conceived of a locking mechanism that may provide an additional locking feature, which may require an even greater force before backout may become an issue than with only a taper lock. Additionally, the locking feature may also provide a positive feedback to the surgeon once the fastener 70 or 170 is properly locked and seated in the appropriate manner, i.e., there may be a distinct snapping sound that alerts the surgeon that the lock has occurred.

It will be appreciated that such a positive feedback to the surgeon, which may be in the form of a snap, may be advantageous because the feedback may correspond to an adequate depth measurement of the fastener 70 or 170 in the bone when inserting said fastener 70 or 170 into said bone. Once the snap occurs, the fastener 70 or 170 may be snap-fit within the through passage 68 or 168 of the receiving member 64 or 164, thereby locking the two components together. When the snap-fit occurs, the snapping sound may indicate that the fastener 70 or 170 is located at an appropriate depth in the bone, and whether to continue insertion of the fastener 70 or 170 should be considered since the depth of said fastener 70 or 170 in the bone may be adequate. It will be appreciated that the depth of the fastener's 70 or 170 threaded engagement with the bone may be solidified once the fastener 70 or 170 snaps into the through passage 168 of the receiving member 164, such that no further insertion may be necessary.

There may be three indications when use of the elongate member 60, the receiving member 64 or 164, and the fastener 70 or 170 may be warranted on the cervical spine, and include: 1) patients who have degenerative problems; 2) patients who have osteoporosis; and 3) patients who have experienced trauma. In today's world, the general population is living longer, but at the same time there are some unhealthy trends developing, such as overeating and smoking, that may lead to increased rates of obesity, type II diabetes as well as other health problems. These problems may lead to increased degeneration and osteoporosis (soft bone) for a larger number of patients. The locking mechanism of the present disclosure was developed to be used with such soft bone, and may not take a large amount of force to form the lock between the fastener 70 or 170 and the receiving member 64 or 164.

The present embodiment illustrated in FIGS. 11-13 may comprise a fastener 170 and a receiving member 164, which may be used in conjunction with the elongate member 60. The fastener 170, illustrated in FIG. 11 as a bone screw, may comprise a first portion 201 and a second portion 202. The first portion 201 may comprise the head 196, wherein the head 196 may comprise a first tapered section 172 and a second tapered section 173. The head 196 may also include a recess 194 (illustrated best in FIG. 13) that may be formed in a top surface 196a of said head 196 for receiving an instrument, which instrument may be configured for driving the fastener 170 into the vertebral bone. It should be noted that the first tapered section 172 may be formed on the full length of the head 196, or the first tapered section 172 may be formed on a portion of the head 196. It will be appreciated that the tapered sections 172 and 173 of the first portion 201 may be located on any suitable section of the fastener 170, including the head 196, such that at least the first tapered section 172 may mate with a sidewall 169 of the receiving member 164, and any such modification is contemplated by, and intended to fall within, the scope of the present disclosure. It will be appreciated that the second tapered section 173 may also engage with the sidewall of the receiving member, although such is not required.

The second portion 202 may comprise a shaft 192 containing threads 190, and a tip 198. It will be appreciated that, as used herein, the fastener 170 may sometimes be referred to as a screw, bone screw, or as a means for attaching the elongate member 60 to at least one human vertebra. The fastener 170 may be a bone screw, bolt, threadless pin, or any other suitable fastener for attaching the elongate member 60 to at least one human vertebra.

The receiving member 164 illustrated in FIGS. 11-13 of the present disclosure may comprise a geometry that allows the shaft 192 of the fastener 170 to be inserted into the bone, and the head 196 of the fastener to form a taper lock and an interference fit with the through passage 168 of the receiving member 164, by applying a minimum amount of force. The result of the locking mechanism of the present embodiment may be that the fastener 170 may not backout from the receiving member 164, which may be secured to, or maintained within, the elongate member 60.

Referring now to FIGS. 12 and 13, it will be appreciated that an embodiment of the receiving member 164 of the present disclosure may comprise a top surface 165, a bottom surface 166, a first diameter D1 and a second diameter D2. The first diameter D1 may be defined as the width of the receiving member 164 at the top surface 165. The second diameter D2 may be defined as the width of the receiving member 164 at the bottom surface 166. It will be appreciated that the second diameter D2 of the receiving member 164 may be larger than the first diameter D1 of the receiving member 164. In other words, the first diameter D1 may have a value that is less than a value of the second diameter D2.

It will be appreciated that a dimension of the first diameter D1 may be within a range of about eighty percent (80%) to about ninety-five percent (95%) of a dimension of the second diameter D2. More specifically, the dimension of the first diameter D1 may be within a range of about eighty-five percent (85%) to about ninety percent (90%) of the dimension of the second diameter D2.

Similar to the other embodiments of the receiving member 64 disclosed herein, the receiving member 164 of the present embodiment may be used in constrained and semiconstrained plate embodiments. Referring particularly to FIG. 12, the sidewall 169 of the receiving member 164 may define the through passage 168. A lip 180 may extend substantially around a perimeter of the through passage 168, essentially defining an opening to, or a constriction of, said through passage 168. It will be appreciated that the lip 180 may, or may not, extend completely around the perimeter of the through passage 168 without departing from the scope of the present disclosure. It will be appreciated that the lip 180 may also be referred to herein as a locking means or a locking portion of the receiving member.

The lip 180 may extend into the opening of the through passage 168 and may comprise a width dimension D3 that may be within a range of about two percent (2%) to about ten percent (10%) of the width dimension D1 of the receiving member 164 at the top surface 165. More specifically, the width dimension D3 of the lip 180 may be within a range of about four percent (4%) to about eight percent (8%), and may be for example about five percent (5%) to about six percent (6%), of the width D1.

Further, the receiving member 164 may comprise a thickness T1, and the lip 180 may comprise a thickness T2. It will be appreciated that the thickness T2 of the lip 180 may be within a range of about five percent (5%) to about fifteen percent (15%) of the thickness T1 of the receiving member 164. More specifically, the thickness T2 of the lip 180 may be about ten percent (10%) of the thickness T1 of the receiving member 164.

It will be appreciated that the receiving member 164 may comprise an outer surface or exterior surface 174 that may be arcuate or curved. The outer surface 174 may serve as a junction to join the top surface 165 and the bottom surface 166 together. Further, it will be appreciated that the curve of the outer surface 174 may, or may not, be a portion or segment of a sphere. For example, the curved outer surface 174 illustrated in FIGS. 12 and 13 is not a portion or segment of a sphere, but is, nonetheless, curved.

The sidewall 169 of the through passage 168 may comprise a single tapered portion 169a, or alternatively, the sidewall 169 may comprise two or more tapered portions, i.e., a first tapered portion 169a and a second tapered portion 169b as illustrated in FIG. 12. It will be appreciated that the first tapered portion 169a of the sidewall 169 may essentially undercut the top surface 165 of the receiving member 164, thereby forming the lip 180. Thus, it will be appreciated that the lip 180 may extend over and partially into the opening of the through passage 168.

It will be appreciated that the sidewall 169 of the receiving member 164, comprising the first tapered portion 169a and the second tapered portion 169b illustrated in FIG. 12, may have a taper angle change, with respect to an axis A-A. In other words, the first tapered portion 169a may have a taper angle that is different from the taper angle of the second tapered portion 169b, although the two tapered portions 169a and 169b may have equal taper angles without departing from the scope of the present disclosure.

More specifically, a cross-section of the first tapered portion 169a reveals that the first tapered portion 169a may have a total included taper angle (both sides of the first tapered portion 169a), with respect to the axis A-A, that may be within a range of about eight (8) degrees to about twenty-four (24) degrees. Applicants have found that a total included taper angle between the range of about twelve (12) degrees to about twenty (20) degrees, and more specifically about sixteen (16) degrees, to be sufficient for the taper angle of the first tapered portion 169a. Stated in another way, the taper angle of a single side of the first tapered portion 169a may be within a range of about four (4) degrees to about twelve (12) degrees, particularly within a range of about six (6) degrees to about ten (10) degrees, and more particularly about eight (8) degrees.

It will be appreciated that the first tapered portion 169a may have a taper angle that is greater than a self-locking morse taper, such that no taper lock may be formed. As indicated above, the first tapered portion 169a may function to provide for a greater lip 180, such that the lip 180 may be formed larger than would otherwise be possible without the first tapered portion 169a undercutting the surface 165. Accordingly, the first tapered portion 169a may, or may not, engage the head 196 of the fastener 170 without forming a self-locking connection due to the associated taper angle.

Additionally, the second tapered portion 169b of the sidewall 169 illustrated in FIG. 12 may comprise a taper angle, with respect to the axis A-A, that may be chosen to be within a range of self-locking taper angles, and more specifically may be a morse taper. For example, a cross-section of the second tapered portion 169b reveals that the second tapered portion 169b may have a total included taper angle (both sides of the second tapered portion 169b) that may be within a range of about two (2) degrees to about seventeen (17) degrees, and more specifically within a range of about four (4) degrees to about sixteen (16) degrees, which ranges have been found to be sufficient to achieve the self-locking result. In other words, the taper angle of a single side of the second tapered portion 169b may be within a range of about two (2) degrees to about eight and a half (8.5) degrees, and more particularly about four (4) degrees. The reason for providing a self-locking taper may be to: (1) keep the head 196 of the fastener 170 from moving completely through the through passage 168 of the receiving member 164, and (2) provide the means for locking the head 196 of the fastener 170 to the sidewall 169 of the receiving member 164.

The receiving member 164 may comprise a surface 182 leading into the through passage 168 from the top surface 165 that may define a portion of the lip 180. The lead-in surface 182 may be formed at an angle relative to the axis A-A of the receiving member 164. It will be appreciated that the lead-in surface 182 may be tapered, and may taper from the top surface 165 toward the bottom surface 166, i.e., in a proximal to distal direction. The lip 180 may be defined by the lead-in surface 182 at the top of the lip 180, and by the first tapered portion 169a of the sidewall 169 at the bottom of the lip 180, which first tapered portion 169a may undercut the top surface 165 of the receiving member 164, thereby forming said lip 180. The lead-in surface 182 may be rounded or curved, i.e., not linear, and may, or may not, completely surround the opening to the through passage 168. However, it will be appreciated that the lead-in surface 182 may be modified to be linear without departing from the scope of the present disclosure.

It will be appreciated that the lip 180 may be configured and dimensioned so as to permit the head 196 of the fastener 170 to enter into the through passage 168. Once the head 196 of the fastener 170 has been fully seated within the through passage 168 of the receiving member 164, the lip 180 may thereafter serve to retain said head 196 of said fastener 170 within the through passage 168. Accordingly, the ability of the fastener 170 to back out of the receiving member 164 may be substantially reduced due to (1) the self-locking taper connection and (2) the retention lip 180.

It will be appreciated that the fastener 170 may inserted into, and attached to, the receiving member 164, such that the head 196 of the fastener 170 may snap-fit into the through passage 168 of the receiving member 164. The snap-fit may occur after the head 196 of the fastener 170 enters the through passage 168. More specifically, the head 196 of the fastener 170 may be configured and dimensioned such that the portion of the head 196 that is immediately adjacent the shaft 192 may be smaller than a top portion of the head 196, which is the portion of the head 196 that is farthest from the shaft 192. Accordingly, a majority of the head 196 may enter through the opening formed by the lip 180, such that only a small portion of the head 196 may actually engage a portion of the lip 180, i.e., the widest portion of the head 196. The minimal amount of contact formed between the head 196 of the fastener 170 and the lead-in surface 182 of the lip 180 may be described as line or band contact. As pressure or force is added to the fastener 170, the head 196 may resiliently force the lip 180 outwardly for a brief moment to allow the passage of the remainder of the head 196. Once the head 196 passes by the lip 180, the lip resiliently snaps back to its original position, thereby snapping the head 196 into the through passage 168.

It will be appreciated that the lip 180 may be formed from a material that exhibits at least some amount of elasticity, such that the lip 180 may be resiliently and elastically deformable, and may not plastically deform. In other words, the lip 180 may expand to permit entry of the head 196 of the fastener 170, but the lip 180 may not expand so far as to deform permanently or plastically. It will be appreciated that the ability of the lip 180 to elastically expand may allow said lip 180 to open and then close back substantially to its original position without plastically deforming.

The lead-in surface 182 may be shaped in a convex manner as illustrated in FIG. 12, or the surface 182 may be linear, without departing from the scope of the present disclosure. Accordingly, the shape of the lip 180 may be convex, as opposed to linear. The result of such a shape may be that only a minimal amount of contact may be formed between the head 196 of the fastener 170 and the lead-in surface 182 of the lip 180. Such a minimal contact may be referred to herein as a line or band of contact. The result of the minimal line contact may be that less frictional forces are present between the lip 180, and specifically the lead-in surface 182, and the head 196 of the fastener 170. In such a situation, because the frictional forces between the components may be less, less force is required to overcome those frictional forces, due to the minimal amount of line contact between the head 196 and the lip 180. Therefore, the shape, and potentially the angle, of the lead-in surface 182 may aid in the ability to form the locking snap-fit.

Whether convex or linear, the angle of the lead-in surface 182 may be different than the taper angle of the first tapered section 172 of the fastener head 196. The result may be that only a minimal amount of force may be necessary to snap and seat the head 196 of the fastener 170 into the through passage 168 of the receiving member 164. Such minimal force may be advantageous for patient's with osteoporosis (soft bone) because the force required to connect the components together may not damage the bone.

If the angle of the lead-in surface 182 were the same as, or substantially equal to, the tapered section 172 of the head 196 of the fastener 170, larger frictional forces may be present therebetween. Because such frictional forces must be overcome to form the desired lock and snap-fit, a larger force may be required than may be necessary when the angle of the lead-in surface 182 is different than the taper angle of the head 196.

Alternatively, the angle of the lead-in surface 182 and the angle of the first tapered section 172 of the head 196 may be substantially equal to each other without departing from the scope of the present disclosure. Further, it will be appreciated that the lip 180 may be dimensioned such that an amount of force required to seat the fastener 170 in the through passage 168 of the receiving member 164 is less than an amount of force required to remove the fastener 170 from said through passage 168 of said receiving member 164.

The receiving member 164 may be geometrically shaped such that it will not flip over itself within the hole 62 of the elongate member 60. The top surface 165 of the receiving member 164 may be substantially smooth so as to not irritate the body's soft tissue, which may come in contact with the top surface 165 of the receiving member 164. The receiving member 164 may further be geometrically shaped such that a substantial corner 175 may be formed at the junction of the outer surface 174 and the bottom surface 166. It will be appreciated that the corner 175 may be curved or rounded, and may have a slight edge break, such that said corner 175 may not be blunt. It will be appreciated that the corner 175 may have about a three thousandths radius. However, it will be appreciated that one of ordinary skill in the art may modify the radius to be more or less than that stated above, without departing from the scope of the present disclosure.

The corner 175 may function to interfere with the lower rim 80 of the hole 62 of the elongate member 60, such that the corner 175 may not flip over itself. In other words, the corner 175 may interfere with, or hit, a ledge manufactured as part of, or within, the hole 62 to inhibit the receiving member 164 from flipping over itself in the hole 62, thereby maintaining the receiving member 164 in a proper orientation within said hole 62 of the elongate member 60. It will be appreciated that a dimension of overlap of the lower rim 80 relative to the discretely curved or rounded corner 175, is at least five thousandths, such that the interference may maintain the receiving member 164 within the hole 62.

It will be appreciated that the curvature of the outer surface 174 of the receiving member 164 may comprise a radius, or an equator. The radius of curvature of the receiving member 164 may comprise an origin 177. A reference line B-B may lie in a plane that is perpendicular to the axis A-A and that passes through a point on the curved outer surface 174 where the slope is zero, such that the intersection of the reference line B-B and the axis A-A defines the origin 177 of the radius of the receiving member 164. It will be appreciated that the location of the origin 177 of the radius of curvature may ultimately be determined by the shape of the outer surface 174.

As illustrated in FIG. 12, the origin 177 may be positioned below a midline of the receiving member 164, which may be designated by the reference line C-C and may be defined as a location on the receiving member 164 that may be equal to the thickness T1 of said receiving member 164 divided in half. In other words, the origin of the radius of curvature may not be centered with respect to the receiving member 164, but may be formed below the midline C-C. The result of the origin 177 placement with respect to the receiving member 164 may be that the outer surface 174 of the receiving member 164 may not be spherical in nature, but may be curved as illustrated in FIG. 12.

At least one reason for shaping the curvature of the receiving member 164 in such a manner and positioning the origin 177 of the radius below the midline C-C may be as follows. When a surgeon positions the elongate member 60 on the patient's bone, the surgeon may not want the receiving member 164 to contact or hit the bone while the receiving member 164 rotates as the fastener 170 enters said bone. This may be because the fastener 170 is designed to be inserted into the bone at a variable angle, and contact between the receiving member 164 and the bone would inhibit the angle variability. Accordingly, the shape of the receiving member 164 may not allow contact with the bone, such that the receiving member 164 may move within the hole 62 to allow angle variability.

The shape of the receiving member 164 may allow said receiving member 164 to be positioned in the hole 62 such that the receiving member 164 may stick out or protrude beyond the top surface 65 of the elongate member 60. Further, the shape of the receiving member 164 may allow the receiving member 164 to rotate and only touch the patient's soft tissue with the smooth, top surface 165 of said receiving member 164. Positioned in that way, the receiving member 164 may not touch the bone on the bottom of the plate 60, when the receiving member 164 and fastener 170 rotate or spin as the fastener 170 enters the bone. It will be appreciated that the shape of the receiving member 164 may allow for a greater taper engagement between the receiving member 164 and the head 196 of the fastener 170, without a loss in fastener 170 angle variability.

As illustrated in FIG. 13, the first portion 172 of the head 196 of the fastener 170 may matingly engage the second portion 169b of the sidewall 169 of the receiving member 164 in a self-locking, tapered engagement. Additionally, another portion of the head 196 may, or may not, engage the first portion 169a of the sidewall 169 of the receiving member 164. It will be appreciated that a primary lock may occur at the site of engagement between surfaces of the first portion 172 of the head 196 of the fastener 170 and the second portion 169b of the sidewall 169 of the receiving member 164. It will be appreciated that a secondary lock may also be implemented at the site of engagement, if any, between surfaces of the other portion of the head 196 and the first portion 169a of the sidewall 169. However, it should be noted that such a secondary lock is not required by the present disclosure.

Further, the lip 180 may function to maintain the head 196 of the fastener 170 within the through passage 168 of the receiving member 164 to thereby reduce the occurrence of fastener backout. More specifically, once the head 196 is seated within the through passage 168 and the snap lock has occurred, the lip 180 may contact the top surface 196a of the head 196 to thereby retain the fastener 170 within the through passage 168, reducing fastener backout.

It will be appreciated that the receiving member 164 may or may not expand as the head 196 enters the through passage 168. If expansion of the receiving member 164 is desired, for example in a constrained embodiment, then the receiving member 164 may comprise at least one slot for facilitating expansion. However, in situations where expansion is not desirable, for example in a semiconstrained embodiment, then the receiving member 164 may not comprise any slots or gaps in the outer surface 174, such that substantially no expansion may occur. It will be appreciated that in the embodiments of the receiving member 64 or 164, where substantially no expansion may occur, some minor amount of expansion may occur in actuality on a micro-level. However, such expansion, if present at all, may be only slight, and may not be readily visible or determinable by the average human observer without the aid of instrumentation.

Figure 14:
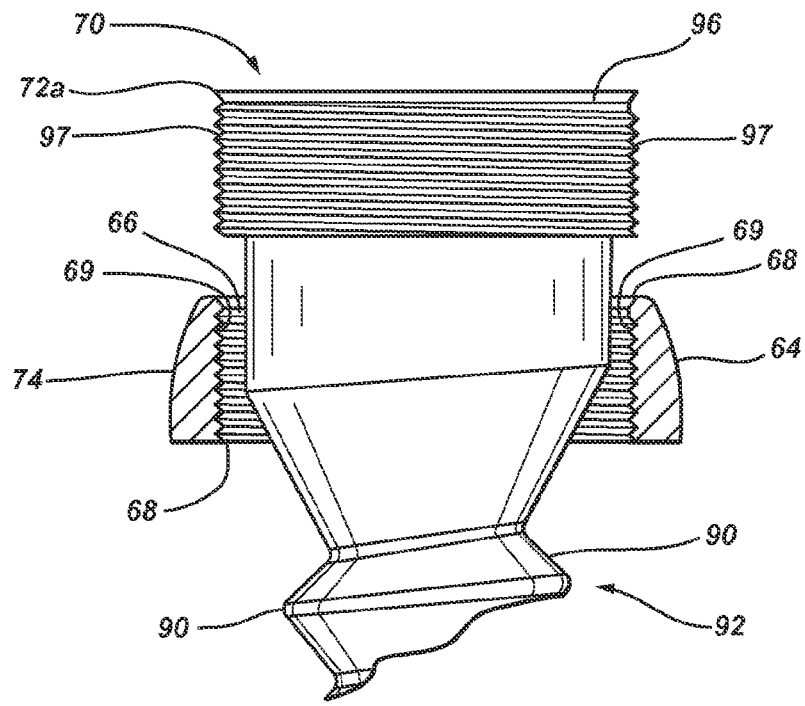
FIG. 14 is a side view of an alternative embodiment of the present disclosure illustrating a fastener, and a cross-sectional view of a receiving member, made in accordance with the principles of the present disclosure.
Figure 15:
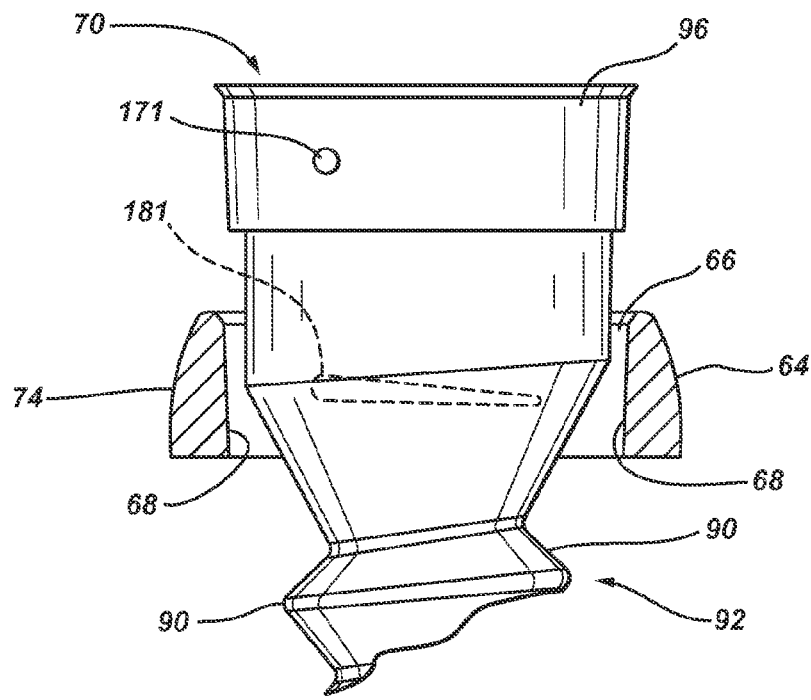
FIG. 15 is a side view of an alternative embodiment of the present disclosure illustrating a fastener, and a cross-sectional view of a receiving member, made in accordance with the principles of the present disclosure.

Referring now to FIGS. 14-15, wherein additional embodiments of a fastener and a receiving member are illustrated. Particularly, FIG. 14 illustrates a partial, cross-sectional view of an alternative embodiment of an apparatus for restricting backout of the fastener 70 from the receiving member 64. As illustrated, the fastener 70 may comprise similar features as already described herein, with the added feature that the head 96 of the fastener 70 may comprise threads 97 on the outer surface 72a of said head 96. Correspondingly, the receiving member 64 may comprise an aperture 66 formed therethrough that may be defined by a sidewall 68. It will be appreciated that the sidewall 68 may comprise threads 69 for matingly engaging the threads 97 of the head 96 of the fastener 70. The threaded engagement may function to provide another mechanism for restricting backout of the fastener 70 from the receiving member 64.

Referring now to FIG. 15, wherein another embodiment of a fastener and a receiving member are illustrated. Particularly, FIG. 15 illustrates a partial, cross-sectional view of an alternative embodiment of an apparatus for restricting backout of the fastener 70 from the receiving member 64. As illustrated, the fastener 70 may comprise similar features as already described herein, with the added feature that the fastener 70 may comprise a protrusion 171 for providing a locking mechanism to restrict backout of said fastener 70 from the receiving member 64. It will be appreciated that the protrusion 171 may be any protrusion that is known, or that may become known, in the art and may be any size, shape or dimension. Further, the receiving member 64 may comprise similar features as described herein, with the added feature of a locking recess 181 formed within the sidewall 68 of the through-passage 66. The shape of the recess 181 may be such that the protrusion 171 of the fastener 70 may enter therein and may be press-fit into said recess 181. In other words, once the protrusion 171 enters the recess 181, i.e., by using a turn, whether a full or partial turn, of the fastener 70 the protrusion 171 may be press-fit into the recess 181 to thereby lock the fastener 70 to the receiving member 64.

It will be appreciated that as the head 96 of the fastener 70 turns, the protrusion 171 may slide and enter into the recess 181 and may be locked therein. Once the protrusion 171 is secured to the recess 181, the fastener 70 may be essentially locked to the receiving member 64, such that continued rotation of the fastener 70 also turns the receiving member 64 as a unit.

It will be appreciated that the above combinations of a fastener 70 and receiving member 64 are only illustrative of the various mechanisms known, or that may become known in the future, in the art to restrict backout of the fastener from the receiving member, and such mechanisms of restricting backout are contemplated by the present disclosure.

A useful method of securing a bone fixation device onto a patient's spine, may include the following steps:

(a) selecting an elongate member comprising a first opening and having a receiving member disposed within said first opening, and locating the elongate member on the patient's spine;

(b) inserting a shaft portion of a fastener through a through passage of a receiving member until the shaft portion engages bone;

(c) advancing the fastener into the bone until a head portion of the fastener engages a locking portion of the receiving member; and (d) advancing the fastener further until the head portion thereof engages the locking portion of the receiving member, to thereby cause said locking portion to resiliently expand and contract responsive to said head portion, such that said locking portion thereby operates to secure said fastener within said through passage in an interference fit.

It will be appreciated that the structure and apparatus disclosed herein are merely examples of a locking means for resiliently expanding and contracting, and it should be appreciated that any structure, apparatus or system for resiliently expanding and contracting which performs functions the same as, or equivalent to, those disclosed herein are intended to fall within the scope of a locking means for resiliently expanding and contracting, including those structures, apparatus or systems for resiliently expanding and contracting which are presently known, or which may become available in the future. Anything which functions the same as, or equivalently to, a locking means for resiliently expanding and contracting falls within the scope of this element.

It will be appreciated that the structure and apparatus disclosed herein are merely examples of a means for retaining a receiving member, and it should be appreciated that any structure, apparatus or system for retaining a receiving member which performs functions the same as, or equivalent to, those disclosed herein are intended to fall within the scope of a means for retaining a receiving member, including those structures, apparatus or systems for retaining the receiving member which are presently known, or which may become available in the future. Anything which functions the same as, or equivalently to, a means for retaining a receiving member falls within the scope of this element.

It will be appreciated that the structure and apparatus disclosed herein are merely examples of a means for attaching the elongate member to at least one human vertebra of the spine, and it should be appreciated that any structure, apparatus or system for attaching the elongate member to at least one human vertebra of the spine, which performs functions the same as, or equivalent to, those disclosed herein are intended to fall within the scope of a means for attaching, including those structures, apparatus or systems for attaching an elongate member to at least one human vertebra of the spine which are presently known, or which may become available in the future. Anything which functions the same as, or equivalently to, a means for attaching an elongate member 60 to the spine falls within the scope of this element.

It will be appreciated that the structure and apparatus disclosed herein are merely examples of a means for receiving a fastener, and it should be appreciated that any structure, apparatus or system for receiving a fastener which performs functions the same as, or equivalent to, those disclosed herein are intended to fall within the scope of a means for receiving a fastener, including those structures, apparatus or systems for receiving a fastener which are presently known, or which may become available in the future. Anything which functions the same as, or equivalently to, a means for receiving a fastener falls within the scope of this element.

Those having ordinary skill in the relevant art will appreciate the advantages provided by the features of the present disclosure. It is a potential feature of the present disclosure to provide a spinal plate for stabilizing the human spine which is simple in design and manufacture. For example, the one-step self locking feature may permit the surgeon to quickly and efficiently insert the fastener into the spine without undue delay. Another potential feature of the present disclosure may include the fastener and the receiving member each having a tapered portion that matingly engage each other to form a quick and efficient self-locking taper connection. It is another potential feature to provide a receiving member with a locking mechanism that may be formed using only minimal force and that may inhibit fastener backout. It is a potential feature of the present disclosure to provide the receiving member that may comprise a lip that may snap-fit over and help to retain the fastener within the receiving member. Another potential feature of the present disclosure may include features of a constrained and semiconstrained plate, each of which may be used with differing patient needs. Yet another potential feature of the present disclosure may include the advantage of using the fastener and the receiving member in several orthopedic situations to secure several different orthopedic devices to a bone, such as a vertebra, tibia, pelvis and other bone. It will be appreciated that the present disclosure may comprise several potential features that may or may not have been enumerated above, but such potential features may yet be part of the present disclosure.

In the foregoing Detailed Description, various features of the present disclosure are grouped together for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An apparatus for restricting backout of a fastener from an elongate member after the fastener has been secured to a bone, the apparatus comprising:

a receiving member having a top surface, a bottom surface, and an outer surface connecting the top surface to the bottom surface, the outer surface defining a curve that extends from the top surface to the bottom surface, the top surface and the bottom surface defining a thickness of the receiving member, wherein the receiving member is configured to be positioned within an elongate member such that the bottom surface of the receiving member is closer to a bottom surface of the elongate member that is configured to face a bone than is the top surface of the receiving member; and a through passage formed between the top surface and the bottom surface of the receiving member, wherein the through passage is defined by a sidewall;

wherein the receiving member comprises a midline between the top surface and the bottom surface that is spaced above the bottom surface by a distance of one half the thickness of the receiving member, wherein the curve defined by the outer surface of the receiving member comprises a radius of curvature, and wherein an origin of the radius of curvature is positioned below the midline such that the origin of said radius of curvature is not centered with respect to said receiving member and such that the receiving member is prevented from extending below the bottom surface of the elongate member independent of an angle between the bottom surface of the receiving member and the bottom surface of the elongate member.

2. The apparatus for restricting backout of claim 1, wherein the receiving member further comprises a lip extending at least partially inward from the sidewall of the through passage, such that the lip extends into said through passage, wherein said lip is formed near the top surface of the receiving member, such that said lip defines an opening to said through passage.

3. A fixation apparatus for stabilizing a plurality of bone segments comprising:

an elongate member having a top surface, a bottom surface, and a first opening formed through the elongate member, wherein the first opening is defined by a sidewall;

a fastener for attaching the elongate member to at least one bone segment; and a receiving member that is insertable into the first opening of the elongate member, the receiving member having a first aperture formed therethrough, wherein the first aperture is defined by a sidewall and wherein the receiving member defines an axis through the first aperture;

wherein the receiving member is dimensioned relative to the first opening of the elongate member such that said elongate member is configured to be connected to said receiving member in a semiconstrained manner when the receiving member is in the first opening of the elongate member, an outer surface of said receiving member being shaped to cooperate with the sidewall of the elongate member to prevent the receiving member from protruding below the bottom surface of the elongate member, irrespective of an orientation of the axis of the receiving member.

4. The fixation apparatus of claim 3, wherein the receiving member comprises a top surface, a bottom surface, and a lip that extends at least partially inward from the sidewall of the first aperture and is configured to contact at least a portion of the fastener when the fastener is within the first aperture and thereby maintain the fastener within the first aperture.

5. The fixation apparatus of claim 3, wherein the receiving member comprises an outer surface, a top surface, and a bottom surface, wherein the receiving member further comprises a substantial corner formed at a junction between the outer surface and the bottom surface.

6. The fixation apparatus of claim 5, wherein the corner is curved and comprises an edge break, such that said corner is not blunt.

7. The fixation apparatus of claim 6, wherein the corner comprises about a three thousandths radius.

8. The fixation apparatus of claim 5, wherein the corner of the receiving member interferes with a portion of the first opening of the elongate member, such that the interference maintains said receiving member in a proper orientation within said first opening.

9. The fixation apparatus of claim 5, wherein the receiving member comprises a midline, wherein the outer surface of the receiving member is curved and comprises a radius of curvature, wherein the radius of curvature comprises an origin that is positioned below the midline of said outer surface of said receiving member, such that the origin of said radius of curvature is not centered with respect to said receiving member.

10. The fixation apparatus of claim 3, wherein the receiving member comprises a top surface, a bottom surface, and a lip that extends at least partially inward from the sidewall of the first aperture and is configured to contact at least a portion of the fastener when the fastener is within the first aperture and thereby maintain the fastener within the first aperture, wherein the lip has a width dimension that is within a range of about two percent to about ten percent of a width dimension of the receiving member at the top surface.

11. The fixation apparatus of claim 10, wherein the width dimension of the lip is within a range of about four percent to about eight percent.

12. The fixation apparatus of claim 10, wherein the width dimension of the lip is about five percent to about six percent.

13. The fixation apparatus of claim 3, wherein the sidewall of the first aperture comprises a first tapered portion and a second tapered portion.

14. The fixation apparatus of claim 13, wherein the receiving member comprises a top surface, a bottom surface, and a lip that extends at least partially inward from the sidewall of the first aperture and is configured to contact at least a portion of the fastener when the fastener is within the first aperture and thereby maintain the fastener within the first aperture, wherein the first tapered portion undercuts the top surface of the receiving member, to thereby form at least a portion of the lip.

15. The fixation apparatus of claim 13, wherein the second tapered portion comprises a total included taper angle within a range of about two degrees to about seventeen degrees.

16. The fixation apparatus of claim 15, wherein the total included taper angle is within a range of about four degrees to about sixteen degrees.

17. The fixation apparatus of claim 13, wherein the first tapered portion comprises a total included taper angle within a range of about eight degrees to about twenty-four degrees.

18. The fixation apparatus of claim 17, wherein the total included taper angle is within a range of about twelve degrees to about twenty degrees.

19. The fixation apparatus of claim 18, wherein the total included taper angle is about sixteen degrees.

20. The fixation apparatus of claim 3, wherein a lip defines an opening to the first aperture, wherein the lip further comprises a lead-in surface leading into the opening of the first aperture, and wherein the lead-in surface tapers in a proximal-to-distal direction from a top surface toward a bottom surface of the receiving member.

21. The fixation apparatus of claim 20, wherein the lead-in surface of the lip is convex.

22. The fixation apparatus of claim 20, wherein the lead-in surface of the lip is linear.

23. The fixation apparatus of claim 3, wherein the receiving member comprises a first diameter and a second diameter, wherein the first diameter has a value that is less than a value of the second diameter.

24. The fixation apparatus of claim 23, wherein the first diameter has a dimension that is within a range of about eighty percent to about ninety-five percent of a dimension of the second diameter.

25. The fixation apparatus of claim 24, wherein the dimension of the first diameter may be within a range of about eighty-five percent to about ninety percent of the dimension of the second diameter.

26. The fixation apparatus of claim 3, further comprising a lip that extends at least partially inward from the sidewall of the first aperture of the receiving member and is configured to contact at least a portion of the fastener when the fastener is within the first aperture and thereby maintain the fastener within the first aperture, wherein the lip is dimensioned such that an amount of force required to seat the fastener in the first aperture of the receiving member is less than an amount of force required to remove the fastener from said first aperture of said receiving member.

27. The fixation apparatus of claim 3, wherein the receiving member comprises a top surface that at least partially defines a top portion of a lip of the receiving member, the lip extending at least partially inward from the sidewall of the first aperture of the receiving member and configured to contact at least a portion of the fastener when the fastener is within the first aperture and thereby maintain the fastener within the first aperture.

28. The fixation apparatus of claim 27, wherein the sidewall of the first aperture undercuts the top surface of the receiving member, thereby forming at least a bottom portion of the lip.

29. The fixation apparatus of claim 3, wherein the receiving member comprises a thickness, and a lip defined by the receiving member comprises a thickness, the lip extending at least partially inward from the sidewall of the first aperture of the receiving member and configured to contact at least a portion of the fastener when the fastener is within the first aperture and thereby maintain the fastener within the first aperture, wherein the thickness of said lip is within a range of about five percent to about fifteen percent of the thickness of said receiving member.

30. The fixation apparatus of claim 29, wherein the thickness of the lip is about ten percent of the thickness of the receiving member.

31. An apparatus for restricting backout of a fastener from an elongate member after the fastener has been secured to a bone, the apparatus comprising:

an elongate member defining an opening;

a fastener configured to secure the elongate member to bone, the fastener comprising a top surface at its proximal end;

a receiving member configured to be received by the opening of the elongate member, the receiving member having a top surface, a bottom surface, and a curved outer surface connecting the top surface to the bottom surface, a through passage formed between the top surface and the bottom surface of the receiving member, wherein the through passage is defined by a sidewall, the receiving member comprising a lip that extends at least partially inward from the sidewall of the through passage, wherein said lip is formed at the top surface of the receiving member such that said lip defines a constriction of said through passage, wherein the receiving member is configured to receive a portion of the fastener within the through passage and wherein the lip of the receiving member is configured to resiliently expand outwardly to an expanded state to permit said portion of the fastener to enter the through passage such that, when said portion of the fastener has been fully received within the through passage, the lip has contracted from the expanded state such that a distal surface of the lip contacts the top surface of the fastener, thereby inhibiting the fastener from moving out of the through passage in a proximal direction.

32. The apparatus for restricting backout of claim 31, wherein the lip has a width dimension that is within a range of about two percent to about ten percent of a width dimension of the receiving member at the top surface.

33. The apparatus for restricting backout of claim 31, wherein the sidewall of the through passage comprises a first tapered portion and a second tapered portion.

34. The apparatus for restricting backout of claim 33, wherein the first tapered portion undercuts the top surface of the receiving member, to thereby form at least a portion of the lip.

35. The apparatus for restricting backout of claim 33, wherein the second tapered portion comprises a total included taper angle within a range of about two degrees to about seventeen degrees.

36. The apparatus for restricting backout of claim 33, wherein the first tapered portion comprises a total included taper angle within a range of about eight degrees to about twenty-four degrees.

37. The apparatus for restricting backout of claim 31, wherein the lip comprises a lead-in surface leading into the constriction of the through passage, wherein the lead-in surface tapers in a proximal-to-distal direction from the top surface toward the bottom surface of the receiving member.

38. The apparatus for restricting backout of claim 37, wherein the lead-in surface of the lip is convex.

39. The apparatus for restricting backout of claim 37, wherein the lead-in surface of the lip is linear.

40. The apparatus for restricting backout of claim 31, wherein a substantial corner is formed at a junction between the bottom surface of the receiving member and the outer surface of said receiving member, wherein the corner of the receiving member is curved and comprises an edge break, such that said corner is not blunt, and wherein the apparatus further comprises an elongate member having a hole defined by a sidewall formed therethrough, and wherein the corner of the receiving member interferes with a portion of the hole, such that the interference maintains the receiving member in a proper orientation within the hole and keeps the receiving member from flipping over itself in said hole.

41. The apparatus for restricting backout of claim 31, wherein the receiving member comprises a midline, wherein the curved outer surface of the receiving member comprises a radius of curvature, and wherein an origin of the radius of curvature is positioned below the midline of said outer surface of the receiving member, such that the origin of said radius of curvature is not centered with respect to said receiving member.

42. The apparatus for restricting backout of claim 31, wherein the receiving member comprises a first diameter and a second diameter, wherein the first diameter has a value that is less than a value of the second diameter.

43. The apparatus for restricting backout of claim 42, wherein the first diameter has a dimension that is within a range of about eighty percent to about ninety-five percent of a dimension of the second diameter.

44. The apparatus for restricting backout of claim 31, wherein the lip is dimensioned such that an amount of force required to seat the fastener in the through passage of the receiving member is less than an amount of force required to remove the fastener from said through passage of said receiving member.

45. The apparatus for restricting backout of claim 31, wherein the lip is formed at least partially by the top surface of the receiving member, and wherein the sidewall of the through passage undercuts the top surface of the receiving member, thereby forming a bottom portion of the lip.

46. The apparatus for restricting backout of claim 31, wherein the receiving member comprises a thickness, and the lip comprises a thickness, wherein the thickness of said lip is within a range of about five percent to about fifteen percent of the thickness of said receiving member.

47. The apparatus for restricting backout of claim 46, wherein the thickness of the lip is about ten percent of the thickness of the receiving member.

48. The apparatus for restricting backout of claim 31, wherein the lip extends into said through passage;
    wherein the lip has a width dimension that is within a range of about two percent to about ten percent of a width dimension of the receiving member at the top surface;
    wherein the sidewall of the through passage comprises a first tapered portion and a second tapered portion;
    wherein the first tapered portion undercuts the top surface of the receiving member, to thereby form at least a portion of the lip;
    wherein the first tapered portion comprises a total included taper angle within a range of about eight degrees to about twenty-four degrees;
    wherein the second tapered portion comprises a total included taper angle within a range of about two degrees to about seventeen degrees;
    wherein the lip further comprises a lead-in surface leading into the opening of the through passage, wherein the lead-in surface tapers in a proximal-to-distal direction from the top surface toward the bottom surface of the receiving member;
    wherein the lead-in surface of the lip is convex;
    wherein a substantial corner is formed at a junction between the bottom surface of the receiving member and the outer surface of said receiving member;
    wherein the corner of the receiving member is curved and comprises an edge break, such that said corner is not blunt;
    wherein the receiving member comprises a midline, wherein the curved outer surface of the receiving member comprises a radius of curvature, and wherein an origin of the radius of curvature is positioned below the midline of said outer surface of the receiving member, such that the origin of said radius of curvature is not centered with respect to said receiving member;
    wherein the receiving member comprises a first diameter and a second diameter, wherein the first diameter has a value that is less than a value of the second diameter;
    wherein the first diameter has a dimension that is within a range of about eighty percent to about ninety-five percent of a dimension of the second diameter;
    wherein the lip is dimensioned such that an amount of force required to seat the fastener in the through passage of the receiving member is less than an amount of force required to remove the fastener from said through passage of said receiving member; and
    wherein the receiving member comprises a thickness, and the lip comprises a thickness, wherein the thickness of said lip is within a range of about five percent to about fifteen percent of the thickness of said receiving member.

49. The apparatus for restricting backout of claim 31, wherein the top surface of the fastener is substantially smooth.

50. The apparatus for restricting backout of claim 31, wherein the top surface of the fastener is substantially planar.

* * * * *